(12) United States Patent
Park et al.

(10) Patent No.: US 6,808,703 B2
(45) Date of Patent: Oct. 26, 2004

(54) LACTOBACILLUS KCTC 0774BP AND ACETOBACTER KCTC 0773BP FOR TREATMENT OR PREVENTION OF OBESITY AND DIABETES MELLITUS

(75) Inventors: Han Oh Park, Choongcheongbuk-Do (KR); Young Bae Bang, Choongcheongbuk-Do (KR); Hea Jung Joung, Choongcheongbuk-Do (KR); Bong Cheol Kim, Choongcheongbuk-Do (KR); Hang Rae Kim, Choongcheongbuk-Do (KR)

(73) Assignee: Bioneer Corporation, Choongcheongbuk-do (KR)

( * ) Notice: Subject to any disclaimer, the term of this patent is extended or adjusted under 35 U.S.C. 154(b) by 0 days.

(21) Appl. No.: 09/855,836

(22) Filed: May 16, 2001

(65) Prior Publication Data

US 2002/0037577 A1 Mar. 28, 2002

(30) Foreign Application Priority Data

May 17, 2000 (KR) ................................ 10-2000-0026379
Aug. 26, 2000 (KR) ................................ 10-2000-0049805

(51) Int. Cl.[7] .......................... A01N 63/00; C12N 1/00; C12N 1/20

(52) U.S. Cl. ................ 424/93.4; 424/93.45; 435/252.9; 435/823; 435/853

(58) Field of Search ............................. 424/93.4, 93.45, 424/93.46; 435/252.9, 823, 853–856, 243, 252.1, 252.5, 261

(56) References Cited

U.S. PATENT DOCUMENTS 4,568,557 A * 2/1986 Becker et al. ............... 426/618
5,234,904 A * 8/1993 Sawada et al. ................ 514/8

FOREIGN PATENT DOCUMENTS

EP        0956867 A1 * 11/1999

OTHER PUBLICATIONS

Kojic et al.; "Analysis of Exopolysaccharide Production by *Lactobacillus casei* CG11, Isolated From Cheese"; Applied and Environmental Microbiology; American Society for Microbiology; vol. 58, No. 12; Dec. 1992; pp. 4085–4088.
Valla et al.; "Isolation and Characterization of A New Extracellular Polysaccharide from A Cellulose–Negative Strain of *Acetobacter xylinum*"; Can. Journal Microbiology; National Research Council of Canada; vol. 23; 1977; pp. 701–709.
Colvin et al.; "The Biosynthesis of Cellulose by *Acetobacter xylinum* and *Acetobacter Acetigenus*"; Can. Journal Microbiology; National Research Council of Canada; vol. 27; 1981; pp. 599–603.

Beniman et al.; "Synthesis of Cellulose From Pyruvate by Succinate–Grown Cells of *Acetobacter xylinum*"; Journal of Bacteriology; vol. 84; 1962; pp. 625–630.
Lin et al.; "Synthesis of Fibrils in Vitro by A Solubilized Cellulose Synthase From *Acetobacter xylinum*"; Science; vol. 230; Nov. 15, 1985; pp. 822–824.
Aloni et al.; "Solubilization of the UDP–Glucose:1, 4$\beta$–$_D$–Glucan 4–$\beta$–$_D$–Glucosyltransferase (Cellulose Synthase) From *Acetobacter xylinum*"; The Journal of Biological Chemistry; vol. 258, No. 7; Apr. 10, 1983; pp. 4419–4423.
Kranenburg et al.; "Genetics and Engineering of Microbial Exopolysaccharides for Food"; Food Biotechnology; pp. 496–504.
Gell–Schutten et al.; "Biochemical And Structural Characterization of the Glucan and Fructan Exopolysaccharides Synthesized by the *Lactobacillus reuteri* Wild–Type Strain and by Mutant Strains"; Applied and Environmental Microbiology; American Society for Microbiology; vol. 65, No. 7; Jul. 1999; pp. 3008–3014.
Looijesteijn et al.; "Regulation of Exopolysaccharide Production by *Lactococcus lactis* Subsp. *Cremoris* by the Sugar Source"; Applied and Environmental Microbiology; American Society for Microbiology; vol. 65, No. 11; Nov. 1999; pp. 5003–5008.
Micheli et al.; "Isolation and Characterization of a Ropy *Lactococcus* Strain Producing the Exopolysaccharide Kefiran"; Applied Microbiology Biotechnology; Springer–Verlag; vol. 53; 1999; pp. 69–74.
Robijn et al.; "Structural Studies of the Exopolysaccharide Produced by *Lactobacillus paracasei* 34–1"; Carbohydrate Research; Elsevier; vol. 285; 1996; pp. 129–139.
Robijn et al.; "Structural Characterization of the Exopolysaccharide Produced by *Lactobacillus acidophilus* LMG9433"; Carbohydrate Research; Elsevier; vol. 288; 1996; pp. 203–218.
Toyosaki et al.; "Screening of Bacterial Cellulose–Producing *Acetobacter* Strains Suitable for Agitated Culture"; Biosci. Biotech. Biochem.; vol. 59, No. 8; 1995; pp. 1498–1502.
Wong et al.; "Genetic Organization of the Cellulose Sythase Operon in *Acetobacter xylinum*"; Proc. Natl. Acad. Sci.; Genetics; vol. 87; Oct. 1990; pp. 8130–8134.

(List continued on next page.)

Primary Examiner—David Naff
Assistant Examiner—Deborah K. Ware
(74) Attorney, Agent, or Firm—Foley & Lardner LLP

(57) ABSTRACT

The present invention relates to microorganisms for the treatment or the prevention of obesity or diabetes mellitus, which reduce the amount of monosaccharide or disaccharide which may be absorbed into human body by converting monosaccharides such as glucose, fructose, galactose et al. and disaccharides into polymeric materials which cannot be absorbed by the intestine, and relates to a pharmaceutical composition containing the said microorganisms. Preferred microorganisms are *Lactobacillus* sp. BC-Y009 and *Acetobacter* sp. BC-Y058.

26 Claims, 8 Drawing Sheets

OTHER PUBLICATIONS

Williams et al.; "Alternative Environmental Roles for Cellulose Produced by *Acetobacter xylinum*"; Applied and Environmental Microbiology; American Society for Microbiology; vol. 55, No. 10; Oct. 1989; pp. 2448–2452.

Brown et al.; "Cellulose Biosynthesis in *Acetobacter xylinum*: Visualization of the Site of Synthesis and Direct Measurement of the In Vivo Process"; Proc. Natl. Acad. Sci.; Cell Biology; vol. 73, No. 12; Dec. 1976; pp. 4565–4569.

Low et al.; "Role of *Streptococcus thermophilus* MR-1c Capsular Exopolysaccharide in Cheese Moisture Retention"; Applied and Environmental Microbiology; Jun. 1998; pp. 2147–2151.

Amikam et al.; "Cyclic Diguanylic Acid and Cellulose Synthesis in *Agrobacterium tumefaciens*" Journal of Bacteriology; American Society of Microbiology; vol. 171, No. 12; Dec. 1989; pp. 6649–6655.

"New Clues Fount to Diabetes and Obesity"; Science; Vol. 283; Mar. 5, 1999; pp. 1423 & 1425.

* cited by examiner

Phylogenetic analysis diagram of Lactobacillus BC-Y009 based on 16s RNA

Phylogenetic analysis diagram of *Acetobacter* BC-Y058 based on 16s RNA sequence

*LACTOBACILLUS* KCTC 0774BP AND *ACETOBACTER* KCTC 0773BP FOR TREATMENT OR PREVENTION OF OBESITY AND DIABETES MELLITUS

FIELD OF THE INVENTION

The present invention relates to microorganisms for preventing or treating obesity or diabetes mellitus, which are capable of reducing an amount of monosaccharides or disaccharides that can be absorbed into the intestine by converting those mono or disaccharides into polymeric materials that cannot be absorbed in the intestines. The present invention also relates to use of the microorganisms for preventing or treating obesity or diabetes mellitus and a pharmaceutical composition containing the microorganisms.

BACKGROUND OF THE INVENTION

Obesity is well known as a chronic disease caused by various factors whose origins have not yet been clearly discovered. It is understood that obesity induces hypertension, diabetes mellitus, coronary heart disease, gall bladder disease, osteoarthritis, sleep apnea, respiratory disorder, endomerial, prostate, breast and colon cancer and the like.

According to the NIH Report (THE EVIDENCE REPORT: *Clinical Guideline on the Identification, Evaluation, and Treatment of Overweight and Obesity in Adults*, 1999, NIH), about 97,000,000 Americans suffer from overweighting and obesesity, and the number of patients of type II diabetes mellitus associated with obesity, reaches about 15,700,000. Moreover, it is reported that about 200,000 people die of diseases associated with obesity each year (Dan Ferber, Science, 283, pp 1424, 1999).

Diabetes mellitus is one of the most widespread chronic diseases in the world, which impose a substantial expense on the public as well as on patients of diabetes mellitus and their families.

There are several types of diabetes mellitus that are caused by various etiological factors and whose pathogenesis is different from each other. For example, genuine diabetes mellitus is characterized by high level of blood glucose and glycosuria, and is a chronic disorder of carbohydrate metabolism due to a disturbance of the normal insuline mechanism.

Non-Insulin-Dependent Genuine Diabetes Mellitus (NIDDM), or the type II diabetes mellitus is found in adults who have insulin-resistance in a peripheral target tissue, despite of normal generation and function of insulin. Non-Insulin-Dependent Genuine Diabetes Mellitus(NIDDM) can be caused by three important metabolic disorders, i.e., insulin-resistance, fucntional disorder of insulin secretion stimulated by nutrients, and overproduction of glucose in liver. Failure to treat NIDDM, resulting in losing control of blood glucose levels, leads to death of patients from diseases such as atherosclerosis, and/or may cause late complications of diabetes, such as retinopathy, nephropathy or neuropathy.

Accompanying diet-exercise therapy, NIDDM therapy uses sulfonylurea and biguanidine compounds to control blood glucose levels. Recently, therapeutic compounds such as metformin or acarbose have been used for treating NIDDM. However, diet-exercise therapy alone or even combined with chemotherapy using such compounds fails to control hyperglycemia in some of the diabetes mellitus patients. In such cases, these patients require exogenous insulin.

Administration of insulin is very expensive and painful to patients, and furthermore, may cause various detrimental results and various complications in patients. For example, incidences, such as, miscalculating insulin dosage, going without a meal or irregular exercise, may cause insulin response (hypoglycemia) and sometimes the insulin response occurs even without any particular reasons. Insulin injection may also cause an allergy or immunological resistance to insulin.

There are several methods for preventing or treating obesity or diabetes mellitus, including diet-exercise therapy, surgical operation and chemotherapy. Diet-exercise therapy involves a low-calorie and low-fat diet accompanying aerobic exercise, but this therapy requiring a regular performance is hard to continue until achieving the goal.

Despite of instant effects, a surgery for physically removing body fat has limitations due to the risk and cost involved in a surgical operation and insufficient durability of the effects.

As one of the most promising therapies currently developed, pharmacotherapy can reduce blood glucose level, inhibit absorption of glucose, strengthen the action of insulin or induce the decrease of appetite. The medicines that have been developed so far use various physiological mechanisms for the prevention and the treatment of obesity and diabetes mellitus.

Some medicines, such as, sulfonylurea, metformin, pioglitazone or thiazolidindione derivatives and the like have been developed to enhance the function of insulin. Although sulfonylurea stimulates insulin-secretion from β-cells in the pancreas, it may accompany side effects, such as hypoglycemia resulting from lowering blood glucose levels under normal levels.

Metformin is mainly used for insulin-nondependent diabetes mellitus patients who fail to recover after diet-exercise therapy. This medicine inhibits hepatic gluconeogenesis and enhances glucose disposal in muscle and adipose tissue. However, it suffers from side effects, such as, nausea, vomiting and diarrhea.

Pioglitazone developed by Takeda in Japan, enhances the function of insulin through increasing susceptibility of cells to insulin (Kobayashi M. et al., Diabetes, 41(4), pp 476–483, 1992).

Beta 3-adreno receptor inhibitor (BRL-35135) known as a medicine that stimulates the decomposition of body fats and that convert body fats into heat with a specific action on adipose cells, also suffers from lowerings blood glucose level.

The inhibitor of a pancreatic lipase (Orlistat produced by Roche of Switzlend) inhibits and/or reduces absorption of body fats by inhibiting pancreatic lipase. It, however, accompanies undersirable inhibition of absorption of fat-soluble vitamin and may also cause breast cancer.

Generally, medicines that decrease appetite affects catecholamine in the brain. However, dexfenfluororamine and fenfluoroamine have side effects of nerve toxicity and valvular heart disease. Also, sibutramine has side effects of increasing heart rate and blood pressure.

α-Glucosidase inhibitor (Acarbose produced by Bayer of Germany), is known as a glucose absorbing inhibitor. Acarbose is pseudo-monosaccharide which competitively inhibits the action of various a-glucosidases existing in microvilli of the gastrointestinal tract. However, taking a large amount of these may induce diarrhea. (W. Puls et al., Front. Horm. Res. 2, 235, 1998).

Amylase inhibitor that inhibit converting carbohydrates into oligosaccharides has been developed to prevent imbalance of metabolism originated from excessive uptake of nutrient. (Sanches-Monge R. et al. Eur. J. Biochem., 183, 0037–40, 1989).

Dietary fiber using diet with a large amount of vegetable fiber is the easiest way to obtain inhibitory effect on obesity by lowering glucose and/or fat amounts absorbed in the intestine. However, such method also involves problems in requiring facility and manpower for the production of dietary fiber with low productivity.

Polymeric materials, such as, isomaltotriose, dextran and pullulan, inhibit the increase of blood glucose level originated from glucose. However, such materials also cause severe side effects. For example, dextran may induce excessive bleeding by delaying a blood coagulation time.

Among said various medicines, dietary fibers are the most useful medicine for prevention or treatment of obesity because no damage to the human metabolism-balance and use natural substances.

Microorganism dietary fiber is produced using microorganisms, such as, *Gluconobacter* sp., *Agrobacterium* sp., *Acetobacter xylinum*, *A. hansenil*, *A. pasteurianus*, *A. aceti*, *Rhizobium* sp., *Alcaligenes* sp., *Sarcina* sp., *Streptococcus thermophilus*, *Lactococcus cremoris*, *Lactobacillus helveticus*, *Lactobacillus bulgaricus*, *Lactobacillus sake*, *Lactobacillus reuteri*, *Lactobacillus lactis*, *Lactobacillus delbrueckii* subsp., *Lactobacillus helveticusglucose* var. *jugurti*, *Leuconostoc dextranicum*, *Bulgariscus* sp., *Campestris* sp., *Sphingomonas* sp.

Dietary fiber produced by these microorganisms is used as stabilizer, thickening agent, emulsifier, hygroscopic agent of various foods and raw materials of cosmetics and pharmaceuticals. Microorganism cellulose, xanthan, acetan, guar gum, locust bean gum, carrageenan, alginate, and agar obtained from seaweed are commercialized.

*Lactobacillus* sp. strain is the major component of normal microbial flora in the human intestines. Its significant roles for maintaining digestive organ and for healthy environment of the vagina, have been well known. [Bible, D. J., ASM News, 54:661–665, 1988; Reid G. and A. W. Bruce, In H Lappin-Scott (de.), Bacterial biofilms, Cambridge University Press, Cambridge, England, p. 274–281, 1995; Reid G., A. W. Bruce, J. A. McGroarty, K. J. Cheng, and J. W. Costerton, clin. Microbiol. Rev., 3:335–344, 1990]. Generally, *Lactobacillus* strain inhabits in digestive organs (*L. acidophilus*, *L. intestinalis*, *L. johnsonii*, *L. reuteri* et al.,), muscosa of the vagina (*L. vanginals*, *L. gasseri*), food (wine-*L. hilgardii*), lactobacillus beverage (*L. kefir*, *L. kefiranofaciens*), cheese (*L. casey*), vinegar (*L. acetotolerance*), the oral cavity (*L. oris*), yeast (*L. sake*, *L. homohiochi*), fruit juice (*L. kunkeei*, *L. mali*, *L. suebicus*), fermented sausages or fish (*L. farciminis*, *L. alimentarious*) et al.

Many people take health complementary food containing a *Lactobacillus* sp. strain in order to maintain healthy intestines and to prevent urogenital tract infection. Recently, in addition to the prevention of the diarrhea, constipation and urogenital tract infection; various probiotic activities of *Lactobacillus*, such as, control of immunity, control of cholesterol level in blood, prevention of cancer, treatment of rheumatism, alleviation of sensitivity on lactose or effect for atopic dermatitis, have been reported and thus, have attracted more attention.

According to the U.S. Public Health Service Guideline, all of the 262 *Lactobacillus* deposited in ATCC are classified as "Bio-safety Level 1," which stands for no potential risk, which has been known up to now, causing diseases in human or animals. There is no harm to human body among approximately 60 strains of *Lactobacillus*.

Recently, there has been a rapid progress in the research for an extracellular dietary fiber produced by *Lactobacillus*. It has been reported that a process of producing dietary fiber in these strains are very complicated because a lot of genes are mediated in the process, and the amount of dietary fiber thus produced are very low (Int. J. Food Microbiol., Mar 3 40:1–2, 87–92, 1998; Current Opinion in Microbiology, 2:598–603, 1999; Appl. Environ. Microbiol., Feb 64:2, 659–64, 1998; FEMS Microbiol. Rev. Apr 23:2 153–77, 1999; FEMS Microbiol. Rev. Sep 7:1–2, 113–30, 1990).

Also, various researches on the synthesis of cellulose by *Acetobacter* sp. which is well known as a microorganism producing dietary fiber, have been performed (Aloni Y., cohen R., Benziman M., Delmer D, J Biological chemistry, 171:6649–6655, 1989; Ascher M., J. Bacteriology, 33:249–252, 1937; Benziman M., Burger-Rachamimv H., J., Bacteriology, 84:625–630, 1962; Brown AM. Journal of Polymer science, 59:155–169, 1962; Brown AM, Gascoigne JA, Nature, 187:1010–1012, 1960; Calvin JR, Planta DP, Benziman M., Padan E, PANS USA, 79:5282–5286, 1982; Dehmer DP. Brown RM Jr., Cooper JB, Lin FC, Science, 230:82–825, 1985).

*Acetobacter* is a strict aerobe but has characteristics of surviving and living under the condition of infinitesimal oxygen, and of being floated to seek for oxygen by means of synthesizing cellulose dietary fiber itself under this condition of infinitesimal oxygen. According to the research regarding the amount and rate of converting glucose into cellulose dietary fiber by *Acetobacter* (Brown et al.: Proc. Natl. Acad. Sci. USA, Vol73 (12), 4565–4569), *Acetobacter* converts glucose into cellulose with the speed rate of 400 mol/cell/hour. This is equivalent to the rate that about 200 g glucose can be converted into cellulose dietary fiber by $4 \times 10^{15}$ cells per an hour.

Although *Acetobacter* that can metabolizes saccharose is rare, *Acetobacter* converting sacchores in glucose, exists in nature (PNAS, 9: pp14–18). Presently, FDA of the United States has approved *Acetobacter xylinum* for synthesizing acetic acid and sorbose, and has classified it as generally safe microorganism (GRAS: Generally Recognized As Safe).

As mentioned above, although there have been various researches and efforts to develop drugs for treatment or prevention of obesity and diabetes mellitus, their results were not satisfactory. Various chemical substances mentioned above, have been developed for treatment of obesity and diabetes mellitus, but still suffer from various side effects. These drugs forcibly discharge body fat together with valuable proteins. Consequently, any one single drug for treatment or prevention of obesity and diabetes mellitus at the origin thereof does not exist yet.

SUMMARY OF THE INVENTION

Therefore, the object of the present invention is to provide microorganisms capable of living within the intestines and converting oligosaccharides produced by the digestive enzymes into non-digestable polysaccharides, and thereby remarkably reducing the amount of oligosaccharide absorbed into the intestines.

Another object of the present invention is to provide a pharmaceutical composition comprising at least one of said microorganisms in an amount effective to prevent or treat obesity and diabetes mellitus and a pharmaceutically acceptable carrier. Another object of the present invention is to provide a method for preventing or treating obesity, diabetes mellitus comprising administering to a subject in need thereof capable of pharmaceutical comprising a method for reducing weight gain, controlling blood glucose level and control absorption of blood lipod.

The microorganisms that can be used for the pharmaceutical composition of the present invention preferably fall within *Acetobacter* genus, *Gluconobacter* genus, *Lactobacillus* genus, and *Acrobacterium* genus, which are capable of living in the intestine and not harmful to human body, and are capable of converting oligosaccharides into polysaccharides that cannot be absorbed into human body. Specifically, the following microorganisms can be used as microorganisms of the pharmaceutical composition of the present invention, such as, *Acetobacter xylinum, A. hansenii, A. pasteurianus, A. aceti, Lactococcus cremoris, Lactobacillus helveticus, L. bulgaricus, L. sake, L. reutari, L. lactis*, the subspecies of *L. delbrueckii, L. delbrueckii* subsp., and a variant form of *L. helveticusglucose*. Preferably, the microorganisms can be used as an active principle of the pharmaceutical composition of the present invention is *Lactobacillus* sp. BC-Y009 (KCTC0774BP) strain or *Acetobacter* sp. BC-Y058 (KCTC0773BP) strain.

The pharmaceutical composition of the present invention may be administered in a form of tablet, capsule, suspension or emulsion, which comprises excipients, pharmaceutically acceptable vehicles and carriers which are selected depending on administration routes. The pharmaceutical formulation of the present invention may further comprises supplemental active ingredients.

Lactose, dextrose, sucrose, sorbitol, mannitol, starch, acacia gum, calcium phosphate, alginic acid salt, treguhkense latex, gelatin, calcium silicate, finecrystalline cellulose, polyvinylpyrolidon, cellulose, water, syrup, methylcellulose, methylhydroxybenzoate and prophylhydroxybenzoate, talc, magnesium stearate or mineral oil may be used as carriers, exipients or diluents in the pharmaceutical composition of the present invention.

In addition, the pharmaceutical composition of the present invention may further comprises lubricants, moisturizer, emulsifier, suspension stabilizer, preservative, sweetener and flavor. The pharmaceutical composition of the present invention may be in a form of an enteric coating formulation produced by various methods which have been publicly known, in order to deliver the active ingredients of the pharmaceutical composition, ie., microorganisms, to the small intestines without degradation by gastric juices in stomach.

Furthermore, microorganisms of the present invention may be administered in a form of capsule prepared by conventional process. For example, standard vehicles and lyophilized microorganisms of the present invention are mixed together and prepared to pellets and then, the pellets are filled into hard gelatin capsules. In addition, the microorganisms of the present invention and pharmaceutically allowable vehicles, for example, aqueous gum, cellulose, silicate or oil are mixed to produce a suspension or emulsion and then, this suspension or emulsion may be filled into soft gelatin capsule.

The pharmaceutical composition of the present invention may be prepared as an enterically coated tablets or capsules for oral administration. The term "the enteric coating" of this application includes all conventional pharmaceutically acceptable coating that has resistance to gastric juice, however, in the small intestines, can disintegrate sufficiently for a rapid release of the microorganisms of the present invention.

The enteric coating of the present invention can be maintained for more than 2 hours in synthetic gastric juice, such as HCl solution of pH 1 at the temperature of 36° C. to 38° C. and desirably, decomposes within 0.5 hours in synthetic intestinal juice, such as KH2PO4 buffer solution of pH 6.8.

The enteric coating of the present invention applies to each tablet with the amount of about 16 to 30 mg, desirably 16 to 25 mg, more desirably 16 to 20 mg. The thickness of enteric coating of the present invention is 5 to 100 $\mu$m, desirably 20 to 80 $\mu$m. The components of the enteric coating are selected appropriately from common polymeric materials which have been publicly well known. The polymeric materials which may be employed for enteric coating of the present invention are enumerated and described in the flowing articles [The Theory and Practices of Industrial Pharmacy, 3rd Edition, 1986, pp. 365–373 by L. Lachman, Pharmazeutische Technologie, thieme, 1991, pp. 355–359 by H. Sucker, Hagers Handbuch der Pharmazeutischen Praxis, 4th Edition, Vol. 7, pp. 739, 742, 766, and 778, (SpringerVerlag, 1971), and Remington's Pharmaceutical Sciences, 13th Edition, pp. 1689 and 1691 (Mack Publ., Co., 1970)]. For example, cellulose ester derivative, cellulose ether and copolymer of acryl and methyl acrylate or maleic acid or phthalic acid derivative may be used in enteric coating of the present invention.

The preferred enteric coating of the present invention are prepared from polymers of cellulose acetate phthals or trimelitate and methacrylic copolymer (for example, copolymer of more than 40% of methacrylic acid and methacrylic acid which contains hydroxyprophyl methylcellulose phthalate or derivatives from ester thereof).

Endragit L 100-55 manufactured by Rohm GmbH of Germany may be used as a raw material for the enteric coating of the present invention.

Cellulose acetate phthalate employed in the enteric coating of the present invention, has about 45 to 90 cP of viscosity, 17 to 26% of acetyl contents and 30 to 40% of phthalate contents. The cellulose acetate trimelitate used in the enteric coating, has about 15 to 21 cS of viscosity, 17 to 26% of acetyl contents, and 25 to 35% of trimelityl contents. The cellulose acetate trimelitate which is manufactured by the Eastman Kodak Company may be used as a material for the enteric coating of the present invention.

Hydroxyprophyl methylcellulose phthalate used in the enteric coating of the present invention has molecular weight of generally 20,000 to 100,000 dalton, desirably 80,000 to 130,000 dalton and has 5 to 10% of hydroxyprophyl contents, 18 to 24% of metoxy contents, and 21 to 35% of phthalyl contents. Cellulose acetate phthalate manufactured by the Eastman Kodak Company can be used as a material for the enteric coating of the present invention.

Hydroxyprophyl methylcellulose phthalate used in the enteric coating of the present invention is HP50 which is manufactured by the Shin-Etsu Chemical Co. Ltd., Japan. The HP50 has 6 to 10% of hydroxyprophyl contents, 20 to 24% of metoxy contents, 21 to 27% of prophyl contents, and molecular weight is 84,000 dalton. Another material for enteric coating manufactured by the Shin-Etsu Chemical Co. Ltd., is HP55. HP55 can also be used as material for the enteric coating of the present invention. The HP55 has 5 to 9% of hydroxyprophyl contents, 18 to 22% of metoxy contents, 27 to 35% of phthalate contents, and molecular weight is 78,000 dalton.

The enteric coating of the present invention is prepared by using conventional methods of spraying the enteric coating solution to the core. Solvents used in the process of the enteric coating are alcohol such as ethanol, ketone such as acetone, halogenated hydrocarbon such as dichloromethane, or the mixture thereof. Softeners such as Di-n-butylphthalate and triacetin are added to the enteric coating solution in the ratio of 1 part coating material to about 0.05 or to about 0.3 part softner.

A spraying process is preferably performed continuously, and the amount of materials sprayed may be controlled depending on the condition of the coating process. Spraying pressure may be regulated variously and, generally, desirable result can be obtained under the pressure of average 1 to 1.5 bar.

"The effective amount" of this specification means the minimum amount of the microorganisms of the present invention, which can reduce the amount of oligosaccharide absorbed into the body through the intestines of mammalian animals. The amount of microorganisms administered into a body with the pharmaceutical composition of the present invention may be adjusted depending on the administration method and the administration subject.

The composition of the present invention may be administered once or more per day on the subject. The unit of administration amount means that it is separated physically and thus is suitable for the unit administration for the human subjects and all other mammalian animals. Each unit contains a pharmaceutically acceptable carrier and the amount of the microorganisms of the present invention which are effective in therapy.

An oral administration unit of an adult patient contains microorganisms of the present invention in an amount, desirably, 0.1 g or more, and the composition of the present invention contains 0.1 to 10 g per one time administration, desirably 0.5 to 5 g. The effective amount of microorganisms of the present invention is 0.1 g per 1 day.

However, the administration amount can vary depending on the weight and the severity of obesity of the patient, supplemental active ingredients included and microorganisms used therein. In addition, it is possible to divide up the daily administration amount and to administer continuously, if needed. Therefore, range of the administration amount does not limit the scope of the present invention in any way.

The "composition" of the present invention means not only as medicinal products but also to serve as functional foods and health complementary foods.

In case of taking the composition of the present invention periodically, microorganisms form colony within the intestines and interrupt absorption of oligosaccharide in the body competitively. Also, non-digestable fibers produced by microorganisms make a healthy condition for other useful microorganisms within the intestines and stimulate the intestinal activity. Consequently, the composition of the present invention functions to treat and prevent obesity and diabetes mellitus.

BRIEF DESCRIPTION OF THE DRAWINGS

The above objects and other advantages of the present invention will become more apparent by describing in detail a preferred embodiment thereof with reference to the attached drawings, in which.

DETAILED DESCRIPTION OF THE PREFERRED EMBODIMENTS

Figure 1:
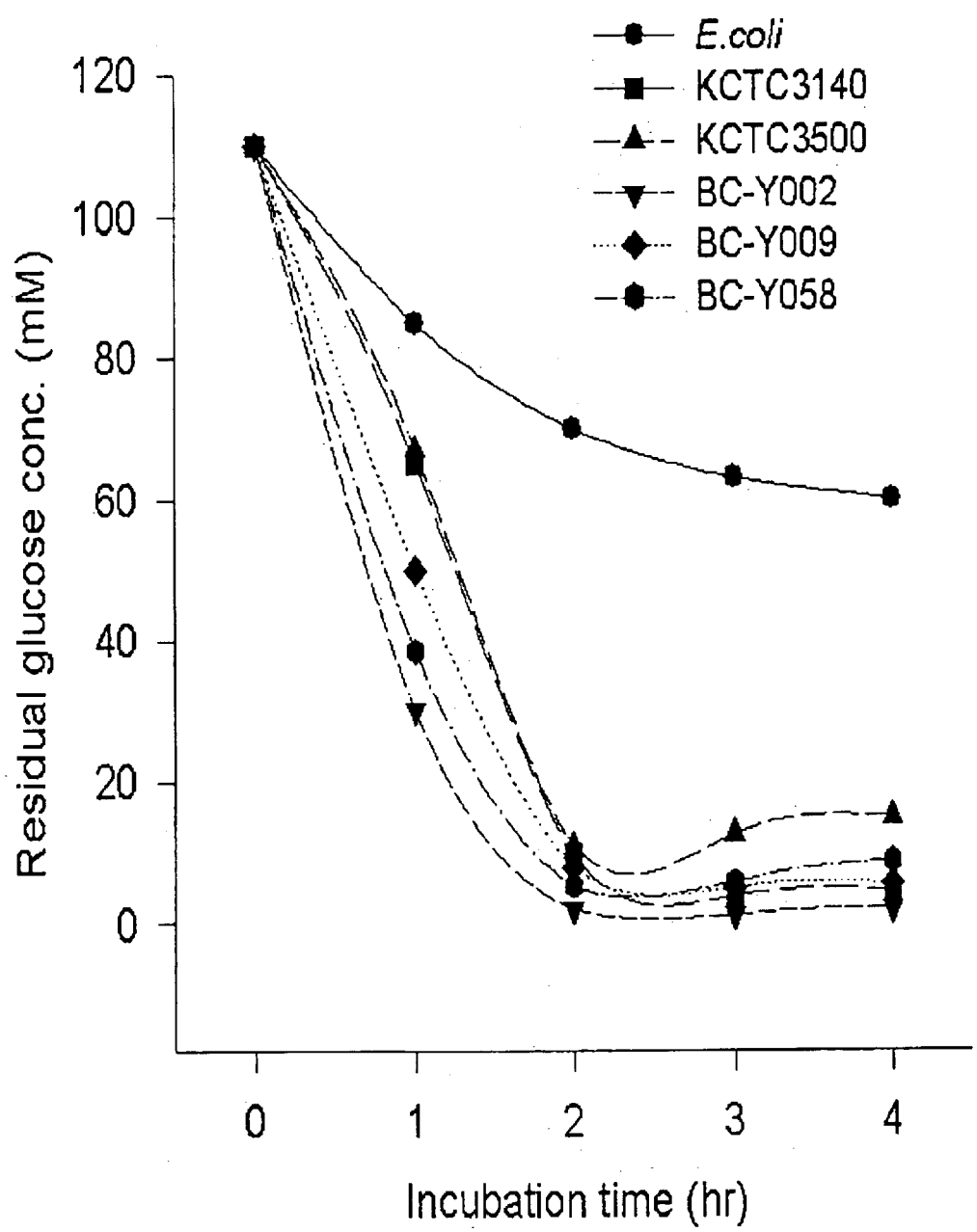
FIG. 1 is the graph illustrating the absorption rate of glucose by the microorganisms of the present invention.

Hereinafter, the present invention will be described more in detail.

The microorganisms which can be used in the pharmaceutical composition of the present invention for preventing and treating obesity and diabetes mellitus, or in a method therefore, should satisfy the requirements of 1) being capable of proliferating within the intestinal layers, 2) being capable of absorbing oligosaccharide rapidly and of converting them into non-digestable or hardly digestable high molecular weight materials, such as fibrous materials, and 3) being harmless to human body and animals. All microorganisms that can satisfy the above requirements can be used as active principles of the pharmaceutical composition of the present invention and for use of the pharmaceutical composition, and may be obtained from the numerous microorganism depository institutions in the world.

Therefore, the microorganisms of the pharmaceutical composition of the present invention are *Acetobacter xylinum*, *Acetobacter* BC-YO58, *Acetobacter hansenii*, *Acetobacter pasteurianus*, *Acetobacter acetic Leuconostoc* sp., *Bacillus* sp., *Lactobacillus* BC-Y009, *Lactobacillus brevis*, *Lactobacillus helveticus*, *Lactobacillus bulgaricus*, *Lactobacillus casei*, *Lactobacillus kefir*, *Lactobacillus keriranofaciens*, *Lactobacillus bifidus*, *Lactobacillus sake*, *Lactobacillus reuteri*, *Lactobacillus lactis*, *Lactobacillus delbrueckii*, *Lactobacillus helveticusglucos* var. *jugurti.*, *Lactococcus cremoris*, *Bifidobacterium bifidium*, *Streptococcus thermophilus* or *Pediococcus* sp. Bacteria, which produce polysaccharide. These microorganisms are described in the following Articles:

Bart Degeest and Luc De Vuyst,

"Indication that the Nitrogen Source Influences Both Amount and Size of Exopolysaccharides Produced by *Streptococcus thermophilus* LY03 and Modelling of the Bacterial Growth and Exopolysaccharide Production in a Complex Medium"

(*Appl. Envir. Microbiol.* 1999, 65: 2863–2870);

Stacy A. Kimmel, Robert F. Roberts and Gregory R. Ziegler,

"Optimization of Exopolysaccharide Production by *Lactobacillus delbrueckii* subsp. *bulgaricus* RR Grown in a Semidefined Medium"

(*Appl. Envir. Microbiol.* 1998, 64: 659–664.);

P. L. Pham, I. Dupont, D. Roy, G. Lapointe and J. Cerning,

"Production of Exopolysaccharide by *Lactobacillus rhamnosus* R and Analysis of Its Enzymatic Degradation during Prolonged Fermentation"

(*Appl Envir. Microbiol.* 2000, 66: 2302–2310.);

Petronella J. Looijesteijn, lngeborg C. Boels, Michiel Kleerebezem and Jeroen Hugenholtz, "Regulation of Exopolysaccharide Production by *Lactococcus lactis* subsp. *cremoris* by the Glucose Source"

(*Appl Envir. Microbiol.* 1999, 65: 5003–5008);

G. H. Van Geel-Schutten, E. J. Faber, E. Smit, K. Bonting, M. R. Smith, B. Ten Brink, J. P. Kamerling, J. F. G. Viegenthart and L. Dijkhuizen, "Biochemical and Structural Characterization of the Glucan and Fructan Exopolysaccharides Synthesized by the *Lactobacillus reuteri* Wild-Type Strain and by Mutant Strains"

(*Appl. Envir. Microbiol.* 1999, 65: 3008–3014.);

G. J. Grobben, I. Chin-Joe, V. A. Kitzen, I. C. Boels, F. Boer, J. Sikkema, M. R. Smith and J. A. M. de Bont, "Enhancement of Exopolysaccharide Production by *Lactobacillus delbrueckii* subsp. *bulgaricus* NCFB 2772 with a Simplified Defined Medium"

(*Appl. Envir. Microbiol.* 1998, 64: 1333–1337.);

Sandrine Petry, Sylviane Furlan, Marie-Jeanne Crepeau, Jutta Cerning and Michel Desmazeaud, "Factors Affecting Exocellular Polysaccharide Production by *Lactobacillus delbrueckii* subsp. *bulgaricus* Grown in a Chemically Defined Mediums"

(*Appl Envir. Microbiol.* 2000, 66: 3427–3431.);

Richard van Kranenburg, Iris I. van Swam, Joey D. Marugg, Michiel Kleerebezem and Willem M. de Vos, "Exopolysaccharide Biosynthesis in *Lactococcus lactis* NIZO B40: Functional Analysis of the Glycosyltransferase Genes Involved in Synthesis of the Polysaccharide Backbone"

(*J. Bacteriol.* 1999, 181: 338–340.);

Deborah Low, Jeffrey A. Ahlgren, Diane Horne, Donald J. McMahon, Craig J. Oberg and Jeffery R. Broadbent, "Role of *Streptococcus thermophilus* MR-1C Capsular Exopolysaccharide in Cheese Moisture Retention"

(*Appl. Envir. MicrobioL* 1998, 64: 2147–2151.);

Richard van Kranenburg and Willem M. de Vos,

"Characterization of Multiple Regions Involved in Replication and Mobilization of Plasmid pNZ4000 Coding for Exopolysaccharide Production in *Lactococcus lactis*"

(*J. Bacteriol.* 1998, 180: 5285–5290.);

F Stingele, JR Neeser, and B Mollet,

"Identification and characterization of the eps (Exopolysaccharide) gene cluster from *Streptococcus thermophilus* Sfi6"

(*J. Bacteriol.* 1996, 178: 1680–1690.);

M Kojic, M Vujcic, A Banina, P Cocconcelli, J Cerning and L Topisirovic,

"Analysis of exopolysaccharide production by *Lactobacillus casei* CG 11, isolated from cheese"

(*Appl. Envir. Microbiol.* 1992, 58: 4086–4088.);

Christian Chervaux, S. Dusko Ehrlich and Emmanuelle Maguin,

"Physiological Study of *Lactobacillus delbrueckii* subsp. *bulgaricus* Strains in a Novel Chemically Defined Medium"

(*Appl Envir. Microbiol.* 2000, 66: 5306–5311.);

J Lemoine, F Chirat, JM Wieruszeski, G Strecker, N Favre and JR Neeser,

"Structural characterization of the exocellular polysaccharides produced by *Streptococcus thermophilus* SFi39 and SFi12"

(*Appl. Envir. Microbiol.* 1997, 63: 3512–3518.);

Bart Degeest and Luc De Vuyst,

"Correlation of Activities of the Enzymes-Phosphoglucomutase, UDP-Galactose 4-Epimerase, and UDP-Glucose Pyrophosphorylase with Exopolysaccharide Biosynthesis by *Streptococcus thermophilus* LY03"

(*Appl Envir. Microbiol.* 2000, 66: 3519–3527.);

Petronella J. Looijesteiin, lngeborg C. Boels, Michiel Kleerebezem and Jeroen Hugenholtz, "Regulation of Exopolysaccharide Production by *Lactococcus lactis* subsp. *cremoris* by the Glucose Source"

(*Appl Envir. Microbiol.* 1999, 65: 5003–5008.);

G. J. Grobben, I. Chin-Joe, V. A. Kitzen, I. C. Boels, F. Boer, J. Sikkema, M. R. Smith and J. A. M. de Bont, "Enhancement of Exopolysaccharide Production by *Lactobacillus delbrueckii* subsp. *bulgaricus* NCFB 2772 with a Simplified Defined Medium"

(*Appl. Envir. Microbiol.* 1998, 64: 1333–1337.);

Richard van Kranenburg, Iris I. van Swam, Joey D. Marugg, Michiel Kleerebezem and Willem M. de Vos, "Exopolysaccharide Biosynthesis in *Lactococcus lactis* NIZO B40: Functional Analysis of the Glycosyltransferase Genes Involved in Synthesis of the Polysaccharide Backbone"

(*J. Bacteriol.* 1999, 181: 338–340.);

Williams WS and Cannon RE,

"Alternative Environmental Roles for Cellulose Produced by *Acetobacter xylinum*"

(*Appl.Envir. Microbiol.* 1989, 55:2448–2452.);

Brown AM and Gascoigne JA,

"Biosynthesis of cellulose by *Acetobacter Acetigenum*"

(*Nature* 1960, 187:1010–1012.);

Carr JG,

"A strain of *Acetobacter aceti* giving a positive cellulose reaction"

(*Nature* 1958, 182:265–266.);

Carr JG and Shimwell JL,

"Old and new cellulose-producing *Acetobacter species*"

(*J. Inst. Brew.* 1958, 64:477–484.);

Colvin JR and Leppard GG,

"The biosynthesis of cellulose by *Acetobacter xylinum* and *Acetobacter acetigenus*"

(*Can. J. Microbiol.* 1977, 23:701–709.);

Colvin JR and Webb TE,

"The variable relation of oxygen consumption to cellulose synthesis by *Acetobacter xylinum*"

(*Can. J. Microbiol.* 1964, 10:11–15.);

Cook KE and Colvin JR,

"Evidence for a Beneficial Influence of Cellulose Production on Growth of *Acetobacter xylinum* in Liquid Medium"

(*Curr. Microbiol.* 1980, 3:203–205.);

Fiedler S, Fussel M and Sattler K,

"Production and application of bacterial cellulose"

(*Zentralbl Mikrobiol.* 1989, 144:473–484.);

Kauri T, Vladuttalor M and Kushner DJ,

"Production of Glycocalyxes by Bacteria Grown in the Presence of Cellulose"

(*Abstract ASM Meeting* 1986, 273);

Mounter LA,

"Observations on the formation and structure of bacterial cellulose"

(*Biochemical Journal* 1951, 50:128–132.);

Valent BS and Albersheim P,

"The effect of pH on binding of xyloglucan to cellulose"

(*Plant Physiol.* 1973, 51 supp.:60.);

Valla S and Kjosbakken J,

"Isolation and characterization of a new extracellular polysaccharide from a cellulose-negative strain of *Acetobacter xylinum*"

(*Can. J. Microbiol.* 1981, 27:599–603.);

Valla S and Kjosbakken J,

"Isolation and characterization of a new extracellular polysaccharide from a cellulose-negative strain of *Acetobacter xylinum*"

(*Can. J. Microbiol* 1981, 27:599–603.);

Valla S, Kjosbakken J and Coucheron DH,

"*Acetobacter xylinum* contains several plasmids: evidence for their involvement in cellulose formation"

(*Archives of Microbiology* 1983, 134:9–11.);

Walker TK and Kaushal R

"Formation of cellulose by *Acetobacter acetigenum*"

(*Nature* 1947, 160:572–573.);

Walker TK and Kaushal R,

"Formation of cellulose by certain species of *Acetobacter*" (*Biochemical J.* 1951, 48:618–621.);

Webb TE and Colvin JR,

"The Variable Relation of Oxygen Consumption to Cellulose Synthesis by *Acetobacter xylinum*"

(*Can. J. Microbiol.* 1964, 10:11–15.);

Webb TE and Colvin JR,

"The extracellular proteins of *Acetobacter xylinum* and their relationship to cellulose synthesis"

(*Can. J. Biochemistry* 1966, 45:465–476.);

Williams WS and Cannon RE,

"Alternative environmental roles for cellulose produced by *Acetobacter xylinium*"

(*Appl. Environ. Microbiol.* 1989, 55:2448–2452.);

Wong HC, etal.,

"Genetic organization of the cellulose in *Acetobacter xylinium*"

(*Proc. natl. acad. sci.* USA 1990, 87:8130–8134.);

Higashimura M, Mulder-Bosman BW, Reich R, Iwasaki T and Robijn GW,

"Solution properties of viilian, the exopolysaccharide from *Lactococcus lactis* subsp. *cremoris* SBT 0495"

(*Biopolymers* 2000, Aug 54:2 143–158.);

Knoshaug EP, Ahigren JA and Trempy JE,

"Growth associated exopolysaccharide expression in *Lactococcus lactis* subspecies *cremoris* Ropy352"

(*J. Dairy Sci.* 2000, Apr 83:4 633–640.);

Micheli L, Uccelletti D, Palleschi C and Crescenzi V,

"Isolation and characterisation of a ropy *Lactobacillus* strain producing the exopolysaccharide kefiran"

(*Appl. Microbiol. Biotechnol.* 1999, Dec 53:1 69–74.);

Looijesteijn PJ, Boels IC, Kleerebezem M and Hugenholtz J,

"Regulation of exopolysaccharide production by *Lactococcus lactis* subsp. *cremoris* By the glucose source"

(*Appl Environ. Microbiol.* 1999, Nov 65:11 5003–5008.);

Smitinont T, Tansakul C, Tanasupawat S, Keeratipibul S, Navarini L, Bosco M and Cescutti P, "Exopolysaccharide-producing lactic acid bacteria strains from traditional Thai fermented foods: isolation, identification and exopolysaccharide characterization"

(*Int. J. Food Microbiol.* Oct. 15, 1999, 51:2–3 105–111.);

Van Kranenburg R, van Swam II, Marugg JD, Kleerebezem M and de Vos WM,

"Exopolysaccharide biosynthesis in *Lactococcus lactis* NIZO B40: functional analysis of the glycosyltransferase genes involved in synthesis of the polysaccharide backbone"

(*J. Bacteriol.* 1999, Jan 181:1 338–340.);

Breedveld M, Bonting K and Dijkhuizen L,

"Mutational analysis of exopolysaccharide biosynthesis by *Lactobacillus sakei* 0–1"

(*FEMS Microbiol. Lett. Dec.* 15, 1998, 169:2 241–249.);

De Vuyst L, Vanderveken F, Van de Ven S and Degeest B,

"Production by and isolation of exopolysaccharides from *Streptococcus thermophilus* grown in a milk medium and evidence for their growth-associated biosynthesis"

(*J. Appl. Microbiol.* 1998, Jun 84:6 1059–1068.);

Low D, Ahlgren JA, Horne D, McMahon DJ, Oberg CJ and Broadbent JR,

"Role of *Streptococcus thermophilus* MR-1C capsular exopolysaccharide in cheese moisture retention"

(*Appl. Environ. Microbiol.* 1998, Jun 64:6 2147–2151.);

Kimmel SA and Roberts RF,

"Development of a growth medium suitable for exopolysaccharide production by *Lactobacillus delbrueckii* ssp. *bulgaricus* RR"

(*Int. J. Food Microbiol. Mar.* 3, 1998, 40:1–2 87–92.);

Duenas-Chasco MT, Rodriguez-Carvajal MA, Tejero-Mateo P, Espartero JL, Irastorza-Iribas A and Gil-Serrano AM, "Structural analysis of the exopolysaccharides produced by *Lactobacillus* spp. G-77"

(*Carbohydr. Res.* 1998, Feb 307:1–2 125–133.);

Espartero JL, Irastorza-Iribas A, Gil-Serrano AM, Duenas-Chasco MT, Rodriguez-Carvajal MA, Tejero Mateo P and Franco-Rodriguez G, "Structural analysis of the exopolysaccharide produced by *Pediococcus damnosus* 2.6"

(*Carbohydr. Res.* Oct. 7, 1997, 303:4 453–458.);

Stingele F, Lemoine J and Neeser JR,

"*Lactobacillus helveticus* Lh59 secretes an exopolysaccharide that is identical to the one produced by *Lactobacillus helveticus* TN-4, a presumed spontaneous mutant of *Lactobacillus helveticus* TY1-2"

(*Carbohydr. Res.* Aug. 7, 1997, 302:3–4 197–202.);

Bubb WA, Urashima T, Fujiwara R, Shinnai T and Ariga H,

"Structural characterisation of the exocellular polysaccharide produced by *Streptococcus thermophilus* OR 901"
(*Carbohydr. Res*. Jun. 11, 1997, 301:1–2 41–50.);

Staaf M, Widmalm G, Yang Z and Huttunen E,

"Structural elucidation of an extracellular polysaccharide produced by *Lactobacillus helveticus*"
(*Carbohydr. Res*. Sep. 23, 1996, 291: 155–164.);

Robijn GW, Gutierrez Gallego R, van den Berg DJ, Haas H, Kamerling JP and Vliegenthart JF, "Structural characterization of the exopolysaccharide produced by *Lactobacillus acidophilus* LMG9433"
(*Carbohydr. Res*. Jul. 19, 1996, 288: 203–218.);

Robijn GW, Wienk HL, van den Berg DJ, Haas H, Kamerling JP and Vliegenthart JF,

"Structural studies of the exopolysaccharide produced by *Lactobacillus paracasei* 34–1"
(*Carbohydr. Res*. May 14, 1996, 285: 129–139.);

Fontaine T, Wieruszeski JM, Talmont F, Saniez MH, Duflot P, Leleu JB and Fournet B, "Exopolysaccharide structure from *Bacillus circulans*"
(*Eur. J. Biochem*. Feb. 26, 1991, 196:1 107–113.);

Osadchaia AI, Kudriavtsev VA and Safronova LA,

"The role of amino acids in intensification of *Bacillus subtilis* exopolysaccharide biosynthesis in deep growth conditions"
(*Mikrobiologiia*. 1995, Jan–Feb;64(1):44–50.); and Mazza P, "The use of *Bacillus subtilis* as an antidiarrhoeal microorganism"
(*Boll. Chim. Farm*. 1994, Jan; 133(1):3–18.), which are hereby incorporated by reference in their entirety, including any drawings, as if fully set forth herein.

In addition, the present inventors have isolated and obtained novel microorganisms which can be used as an active principle of the pharmaceutical composition of the present invention.

In order to isolate and obtain novel microorganisms which satisfy the requirements for an active principle of the pharmaceutical composition of the present invention, the present inventors have researched as follows:

Samples of microorganisms collected from the glucose factory sewage and other locations were inoculated in MRS and BHS agar mediums containing cycloheximide, and then cultured. Colonies formed in agar medium were then inoculated into MRS and BHS liquid medium and incubated without shaking. Microorganisms that formed a matrix or a membrane shape on top layers of the medium were selected. Formed membranes were separated and tested for whether or not the separated membranes were decomposed by the intestinal digestive enzyme. The results determined whether non-digestable (or hardly digestable) high molecular-weight compounds were produced or not. Among the microorganisms, BC-Y009 and BC-Y058 were selected for their high productivity of extracellular polysaccharide (dietary fiber).

Upon observing the morphology of BC-Y009 and BC-Y058 and comparing with 16s rRNA's partial DNA sequences, it was confirmed that each showed high percentage of homology sequence when compared with *Lactobacillus* and *Acetobacter*. Based on the phenotype and 16s rRNA DNA sequence analysis, it was ascertained that BC-Y009 is a novel microorganism which falls within the *Lactobaccilus* genus and BC-Y058 as a novel microorganism of *Acetobacter* genus.

*Lactobacillus* BC-Y009 and *Acetobacter* BC-Y058 of the present invention were administered into a mouse which was induced to have obesity and diabetes mellitus. The blood glucose level of a subject mouse had been decreased approximately 70% after administration.

According to these results, it was confirmed that microorganisms of the present invention has an effect in decreasing blood glucose level and thus it is effective for treating and preventing against diabetes mellitus.

When microorganisms of the present invention, BC-Y009 and BC-Y058 were administered into a mouse induced to have diabetes mellitus and obesity, the feed consumption rate increased 17 to 24% upon comparison with a control mouse. However, weight gain versus feed consumption amount was decreased. The result thus indicates that the microorganism composition of the present invention allows for humans to consume without worrying about obesity or diabetes mellitus.

From the observation that a blood lipid level is also lower than that of control group in case of taking these microorganisms, the microorganisms of the present invention is found to be capable of controlling the occurrence of diabetes mellitus, obesity and circulatory diseases, for example, arteriosclerosis or myocardial infarction. Additionally, in case of a normal mouse, mouse administered with the composition of the present invention consumed more feed, thus energy efficiency had been decreased in comparison with a control mouse. However, it was confirmed that there was no side effects led from the administration upon observing that the change of lipid content was negligible.

Hereinafter, the present invention will be further explained with reference to the following examples. The examples are given only for illustration of the invention and are not intended to limit the scope of the present invention.

EXAMPLE 1

Selecting of microorganism which produces extracellular polysaccharide from samples In order to isolate microorganisms which produce dietary fibers, samples were collected from glucose factory sewage and other locations. 10 g of the mixture thus collected were disrupted and suspended in 90 ml of physiological saline solution (0.85% NaCI). The said suspended samples were diluted to $10^{-2}$, $10^{-4}$, and $10^{-6}$ in physiological saline solution. These diluted samples then smeared on MRS agar medium containing 1 mg of cycloheximide per 100 ml medium (1% Peptone, 1% beef extract, 0.5% yeast extract, 2% glucose, 0.1% Tween-80, 0.2% Citric Acid Ammonium, 0.5% Sodium Acetate, 0.01% $MgSO_4$, 0.005% $MnSO_4$, 0.2% Sodium Phosphate pH6.5) and on BSH agar medium (2% glucose, 0.5% Peptone, 0.5% yeast extract, 0.27% Na2HPO4, 0.115% Citric Acid pH 5.0)(Hestirin and Schramm, J. Gen. Microbiol., 11:123, 1954) and cultured in 30° C. for 72 hours. Approximately 2,000 colonies were selected and were initially inoculated in 5 ml MRS liquid medium and BSH liquid medium at 30° C. for 72 hours and cultured without shaking. The microorganism which form a membrane shape on upper layer of the liquid medium and the microorganism which form capsule-shaped extracellular polysaccharide and of which medium was transparent, were selected. These microorganisms were inoculated again in 5 ml of MRS liquid medium and BSH liquid medium and stirred at 30° C. and the absorbance thereof was measured at 600 nm by spectrophotometer. Microorganisms were diluted with BSH liquid medium until the absorbance thereof reached to 0.2. 10 ml of microorganism thus diluted was inoculated into 100 ml of BSH liquid medium at 30° C. for 72 hours and cultured without shaking.

In order to measure the amount of extracellular polysaccharide (dietary fibers) thus produced, each medium were centrifuged at 6,000 rpm in 4° C. to obtain the precipitation of microorganisms. Cell membrane were disrupted by alkali lysis in 0.1 N NaOH solution and left alone in 800° C. for 30 minutes and centrifuged at 6,000 rpm in 4° C. and repeated multiple times, the above process in entirety. Extracellular polysaccharide entangled like white strings were isolated and lyophilized to be measured the amount thereof. Microorganisms with high extracellular polysaccharide productivity were selected and extracellular polysaccharide productivity was compared with each other (Table 1).

TABLE 1

Comparison of extracellular polysaccharide productivity

| Selection Number | Amount of produced extracellular polysaccharide (dry weight g/l BSH) |
|---|---|
| BC-Y 009 | 3.8 |
| BC-Y 002 | 4.2 |
| BC-Y 015 | 3.2 |
| BC-Y 026 | 4.1 |
| BC-Y 058 | 4.8 |
| BC-Y 112 | 3.0 |
| BC-Y 130 | 3.4 |
| BC-Y 201 | 3.3 |

EXAMPLE 2

The morphological determination and characteristics of the selected BC-Y009 and BC-Y058

Microorganisms which show high polysaccharide productivity selected from the Example 1 were BC-Y009, BC-Y002, BC-Y01 5, BC-Y026, BC-Y058, BC-Y112, BC-Y130, and BC-Y201. Upon observing partial DNA sequences, BC-Y009, BC-Y002, BC-Y015 and BC-Y026 were microorganisms of *Lactobacillus* genus, and BC-Y058, BC-Y112, BC-Y130 and BC-Y201 were microorganisms of *Acetobacter* genus.

Among these bacteria, BC-Y009 and BC-Y058 which show high polysaccharide productivity were inoculated in MRS and BSH liquid mediums at 30° C. for 72 hours and cultured in suspension. Cultured mediums were centrifuged at 6,000 rpm in 4° C. to obtain microorganisms and the nucleic acids thereof were isolated by means of using the CTAB/NaCl method. By using 16s rRNA consensus primer, 16s rRNA was amplified by means of PCR method, and the sequence thus obtained, was determined. BLAST analysis (NCBI, USA) on the sequence thus determined, was performed and its result showed high percentage of sequence homology with sequence of *Lactobacillus hilgardii, Acetobacter xylinum, Gluconobacter* sp., numerous other *Lactobacillus* sp. and *Acetobacter* sp. (Tables 2 and 3).

TABLE 2

Comparison of 16S rRNA nucleotide sequence of Lactobacillus sp. BC-Y 009

| | BC-Y009 | L.delbrueckii sub sp. ATCC9649 | L.helveticus NCDO2712T | L.acidophillus ATCC4356 | L.hilgardii NCDO264 | Lactobacillus sp. ATCC13133 |
|---|---|---|---|---|---|---|
| BC-Y009 | — | 145 | 136 | 146 | 3 | 4 |
| L.delbrurckii sp. ATCC9649 | 88.93 | — | 76 | 73 | 142 | 143 |
| L.helveticus NCDO2712T | 89.16 | 93.94 | — | 21 | 134 | 134 |
| L.acidophillus ATCC4356 | 88.85 | 94.43 | 98.33 | — | 144 | 144 |
| L.hilgardii NCDO264 | 99.77 | 89.07 | 89.26 | 88.93 | — | 1 |
| Lactobacillus sp. ATCC13133 | 99.69 | 88.97 | 89.21 | 88.90 | 99.92 | — |

Among 1,400 base pairs which are included in comparison, top right of table indicates number of base pairs which show difference, bottom left of table indicates % homology

TABLE 3

Comparison of 16S rRNA nucleotide sequence of Acetobacter sp. BC-Y 058

| | BC-Y 058 | A.diazotrificus | A.liafaciens | A.hansenii | A.xylinum | A.europaeus |
|---|---|---|---|---|---|---|
| BC-Y 058 | — | 37 | 34 | 10 | 13 | 14 |
| A.diazotrificus | 97.20 | — | 17 | 37 | 35 | 36 |
| A.liafaciens | 97.42 | 98.71 | — | 34 | 32 | 33 |
| A.hansenii | 99.24 | 97.20 | 97.42 | — | 15 | 16 |
| A.xylinum | 99.02 | 97.35 | 97.58 | 98.86 | — | 3 |
| A.eurapaeus | 98.94 | 97.27 | 97.50 | 98.79 | 99.77 | — |

Among 1,320 base pairs which are included in comparison, top right of table indicates number of base pairs which show difference, bottom left of table indicates % homology BC-Y009 is a gram-positive bacteria and 0.5 to 3.0 μm in size. It is a non-motile & short-rod shaped bacteria. It does not form spores and is facultative anaerobic. The growth temperature is between 20° C. to 37° C. and pH level is 2.0 to 8.0 and optimal pH level is 4.0 to 7.0. The experimental results showed that this microorganism was condensed in milk and was negative (non-reactive) to catalase and formed white colored colony in complex medium. It was precipitated in MRS liquid medium and BSH liquid medium in form of white colored capsule. The turbidity of the liquid medium was clear and the microorganism produced extracellular polysacchardie in clear medium and in case liquid medium was shaken, the extracellular polysaccharide (dietary fiber) were broken into small particles.

BC-Y058 is a gram-negative bacteria, rod shaped bacteria and 0.6 to 0.8 μm in size and exists as single or a pair. It is also a non-motile and does not form spores. Growth rate thereof is slow, therefore 5 to 7 days of incubation time is needed and colonies formed are small and hard. In liquid medium, clear cellulose pellicle is formed. Ethanol, acetic acid, or lactic acid can be used as substrates and showed positive response to catalase. This microorganism produces acid by using glucose and in Hoier medium, it can not grow.

Upon consideration of the result of analysis of phenotype and 16s rRNA DNA sequence, BC-Y009 was named as *Lactobacilus* sp. BC-Y009 and BC-Y058 as *Acetobacter* sp. C-Y058. They were deposited in KCTC(Korean Collection for Type Cultures, locate at Korea Research Institute of Bioscience and Biotechnology (KRIBB), #52, Oun-dong, usong-ku, Taejon, 305–333, Republic of Korea) on May 30, 2000, and the deposit num er was granted as KCTC BC-Y009, KCTC BC-Y058, respectively.

EXAMPLE 3

The degree of decomposition of extracellular polysacchride (dietary fiber) by intestinal digestive enzymes In order to determine whether or not dietary fiber produced by said microorganisms is decomposed by intestinal digestive enzyme, 1 g of porcine pancreatin that shows the activity of 3×U.S. Pharmacopia (manufactured by Sigma) and comprises amylase, lipase, protease and nuclease, was suspended in buffer solution (pH7.5) of 1 g of dried dietary fiber. This suspension was incubated for 7 days at 40° C. and the suspension was collected once a day and the glucose therein was analyzed quantitatively by using DNS(3,5-dinitrosalicylic acid). The result thereof showed that dietary fibers has never been decomposed at all.

Therefore, it was confirmed that the dietary fibers produced by the microorganisms of the present invention do not decompose within the intestine.

EXAMPLE 4

Glucose absorption rate of bacteria

Glucose absorption rates of *Lactobacillus acidophilus* (KCTC3140), *L. hilgardii* (KCTC3500) known as probiotics, and the said *Lactobacillus* BC-Y009, *Acetobacter* BC-Y002, *Acetobacter* BC-Y058 and *E. coli*., were measured in the condition of the intestine. The results are represented in FIG. 1 and Table 4.

As illustrated in FIG. 1 and Table 4, the microorganisms of the present invention are superior to the other lactic acid bacteria in terms of glucose absorption rate.

TABLE 4

Glucose concentration decreased by the bacteria of unit O.D. per unit time.

|  | initial O.D. 600 nm | initial glucose concentration (mM) | glucose concentration after 1 hour (nM) | glucose concentration decreased per unit time and unit O.D. (mM/hr/O.D.) |
| --- | --- | --- | --- | --- |
| E.coli | 3.0 ± 0.1 | 110 | 85 ± 0.5 | 8.3 ± 0.44 |
| BC-Y009 | 3.0 ± 0.2 | 110 | 50 ± 0.3 | 20 ± 1.5 |
| BC-Y002 | 3.0 ± 0.1 | 110 | 30 ± 0.7 | 26.6 ± 1.1 |
| BC-Y058 | 3.0 ± 0.2 | 110 | 38.6 ± 0.3 | 23.8 ± 0.1 |
| KCTC3500 | 3.0 ± 0.2 | 110 | 67.2 ± 0.3 | 14.2 ± 0.4 |
| KCTC3140 | 3.0 ± 0.1 | 110 | 65.2 ± 0.4 | 14.4 ± 0.1 |

EXAMPLE 5

Concentration and survival rate of microorganisms in the intestine after adminstering microorganisms Mouse C57BL/6J Lep$^{ob}$ ob/ob genetically induced of obesity and diabetes mellitus (hereinafter,"OB Mouse"), was starved for 18 hours and fed the composition of the present invention (the number of microorganism of the composition was $1.0 \times 10^{13}$ CFU/g) containing 1% of *Lactobacillus* BC-Y009, *Acetobacter* BC-Y058 (w/w, drying weight) for 7 days, and then the bacterial concentration in the duodenum, the jejunum, and the large intestine of these mice were analyzed. In addition, the bacterial concentration in the duodenum, the jejunum, and the large intestine of the control OB mouse that had been fed the feed without containing the microorganisms of the present invention, was analyzed.

In order to measure the amount of *Lactobacillus*, the duodenum, the jejunum, and the large intestine of the mouse that had been fed *Lactobacillus* feed and the control mice were cut out. Each surfaces of the organs were rinsed with physiological saline solution and the contents were suspended in physiological saline solution. Then, inoculated in MRS agar medium and incubated at 37° C. Three (3) days later, the amount of bacteria was measured by counting floc and by subtracting the amount of *Lactobacillus* in the control group to determine the change of the amount of bacteria (Table 5).

In order to confirm the existence of *Acetobacter*, the each organs of mouse were cut out, then rinsed the surfaces of the organs with physiological saline solution. The contents were suspended in physiological saline solution, then inoculated in BSH liquid medium and cultured at 37° C. for 3 days. By checking the pellicle appeared on top layer of the liquid medium, the existence of fiber-producing *Acetobacter* was confirmed (Table 6).

According to the results represented in Table 5 and Table 6, the said two kinds of microorganisms were both able to proliferate in the intestine.

TABLE 5

The amount of Lactobacillus sp. in the duodenum, the jejunum, and the large intestine of mouse

| the region of intestine | weight (g) | bacterial number (CFU/g) | Existence of membrane formation |
|---|---|---|---|
| Duodenum | 0.18 ± 0.03 | 83 ± 20 | no |
| Jejunum | 0.29 ± 0.05 | $1.2 \times 10^3$ ± 50 | no |
| large intestine | 0.36 ± 0.07 | $5.1 \times 10^3$ ± 30 | yes |

TABLE 6

The amount of Acetobacter sp. in the duodenum, the jejunum, and the large intestine of mouse

| the region of intestine | weight (g) | existence of membrane formation |
|---|---|---|
| duodenum | 0.20 ± 0.02 | no |
| jejunum | 0.28 ± 0.04 | yes |
| large intestine | 0.35 ± 0.03 | yes |

EXAMPLE 6

The change in blood glucose level upon feeding of BC-Y009 and BC-Y058

100 g of mouse feed purchased from SAMYANG Co. and 400 g of Korean rice were mixed to make a composition in which carbohydrate content was 60%, then 5 g of dried Lactobaccillus BC-Y009 or *Acetobacter* BC-Y058 were added thereto to prepare a lyophilized tablet. Mice were fed this tablet with water.

All mice tested in this Example were female and OB mice. *Acetobacter* feed group (OB-058), *Lactobacillus* feed group (OB-009), and the control group (OB-con, which has no microorganism of the present invention in the feed) were bred separately. The breeding condition was that there was light every 12 hour intervals(9:00–21:00 lighted, 21:00–9:00 no lighted) and maintained 20 to 24° C. and 40 to 60% humidity.

Additionally, enteric coating solution was sprayed on dried *Lactobacillus* BC-Y009 or *Acetobacter* BC-Y058 to produce the compostion of the present invention which comprises enteric coated microorganisms. The weight of the enteric coating of material on the composition was approximately 16 to 30 mg or less per tablet. The materials for the enteric coating were selected from common high molecular weight materials, such as, cellulose acetate phthalate, trimelitate, copolymer of methacrylic acid (Methylacrylic acid 40% or more, especially methylacrylic acid including hydroxypropyl methylcellulose phthalate and its ester derivatives), or mixture thereof.

Methylacrylate used in the Example was Endragit L 100-55 manufactured by Rohm GmbH(Germany), cellulose acetate phthalate with about 45 to 90 cP of viscosity, 17 to 26% of acetyl content and 30 to 40% of phthalate content, or cellulose acetate trimelitate manufactured by the Eastman Kodak Company (approximately 15 to 20 cS of viscosity, 17 to 26% of acetyl content and 25 to 35% of trimelityl content).

The enteric coating was produced by a conventional coating process wherein the enteric coating solution was sprayed on a core. Ethanol and acetone mixture was used as solvent and a softening agent was added to the coating solution in a ratio of 1 to approximately 0.005 or 0.3.

The enteric coating composition of the present invention produced by means of the process was provided to the mice with water for unrestricted taking. The blood glucose level of the mouse which has taken the enteric coating composition, was measured.

Before measuring the blood glucose level of each mouse group, each mouse was starved for 18 hours. Following 60 minutes after starvation, sufficient amounts of feed were provided and after a 60 minute period, serum was collected from the retroorbital venous plexus by using anti-coagulating agent-free capillary tubes.

The blood glucose level was measured by absorbance at 505 nm, using the Trinder kit (Cat. 315-500, Sigma, USA) which employs enzyme coloring method. The statistical error of the results was indicated by average ± standard deviation per experimental group, and statistical significance of the average difference in each group was tested through ANOVA ($p<0.02$).

Figure 2:
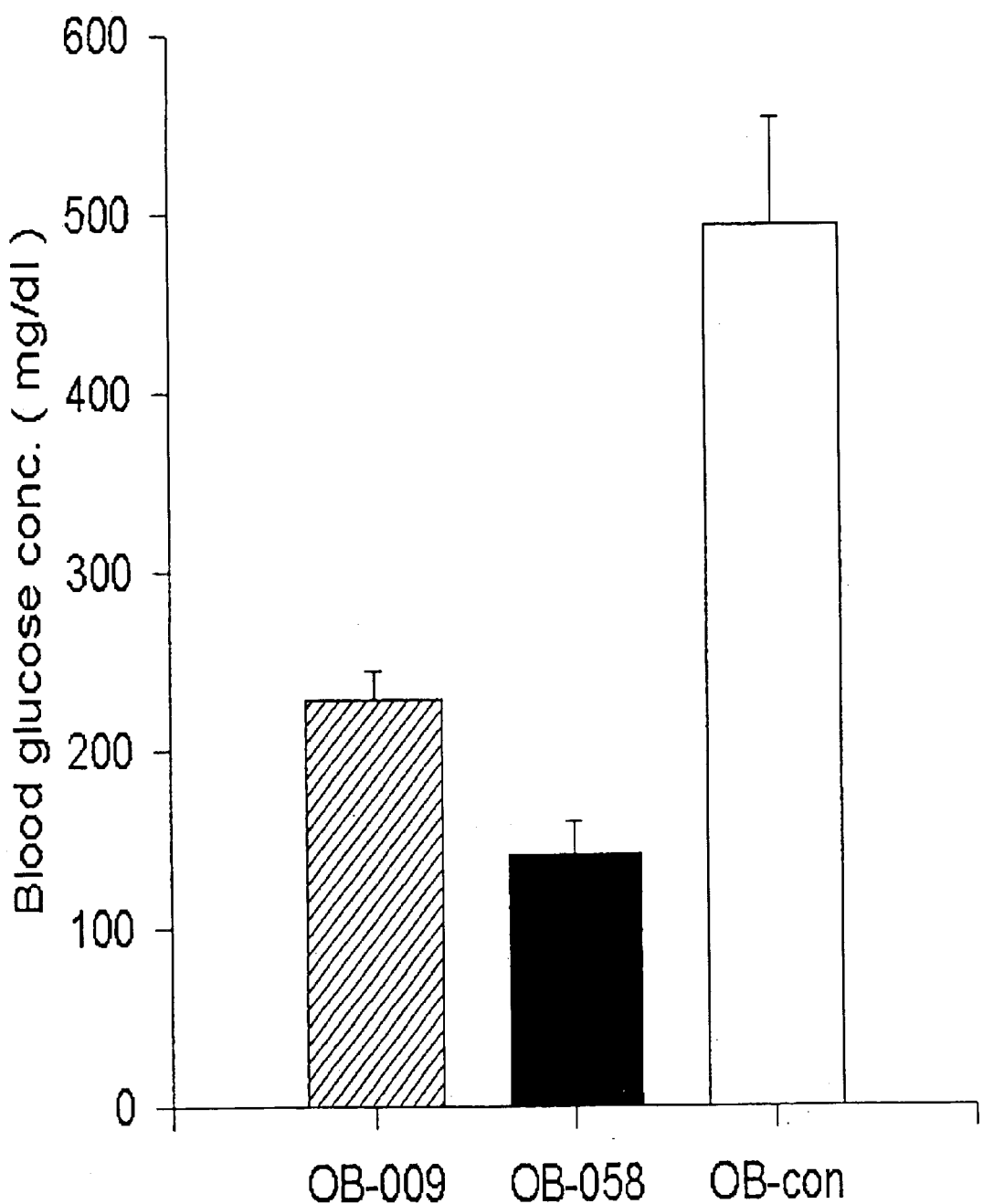
FIG. 2 is the graph illustrating the change of blood glucose level after taking the microorganisms of the present invention.

Data for blood glucose level are illustrated in FIG. 2. As illustrated in the FIG. 2, the blood glucose level for OB-con group is approximately 500 mg/dl, whereas OB-058 blood glucose level is low. Additionally, due to administration of *Acetobacter* BC-Y058 and *Lactobacillus* BC-Y009, the blood glucose levels of each mouse had been decreased to approximately 70% and 53% each (Table 7).

TABLE 7

The change of blood glucose level after administration of *Acetobacter* BC-Y058 and *Lactobacillus* BC-Y009

| | OB-009 | OB-058 | OB-con |
|---|---|---|---|
| Blood glucose level(mg/dl) | 229 ± 16 | 141 ± 19 | 492 ± 60 |

EXAMPLE 7

The change of weight and amount of diet due to taking BC-Y058 and BC-Y009 and in metabolic efficiency Mice were classified as OB-058 group, OB-009 group, OB-con group, and *Acetobacter* BC-Y058 and *Lactobacillus* BC-Y009 were administered on each group and the weight of each mouse was measured in weekly intervals. Along with the measuring of changes in weight, the weight of feed consumed by the mice was also measured, therefore changes of metabolic efficiency of each group were investigated.

The difference of weight change was apparent in each species whose genetic characteristics were different, but the difference of weight change, within the group having the same genetic characteristics was negligible.

As indicated in Table 8, the weight change of OB mice within the period of 7 weeks, regardless of the administration of *Acetobacter* BC-Y058 or *Lactobacillus* BC-Y009, was approximately 47% increase of weight. However, on the contrary, as indicated in Tables 9 and 10, feed consumption percentage, depending on microorganism administration, increased 17 to 24% in OB mice group.

That is, the weight increase of the mice fed feed which comprises the microorganisms of the prevent invention was the same as that of the mice fed that does not contain the microorganism of the prevent invention. The results indicate that because *Acetobacter* BC-Y058 and *Lactobacillus* BC-Y009 suppress increase of blood glucose levels after meal, increase of feed consumption occurs as its compensation. In other words, with the same amount of feed, increase of weight can be decreased by feeding the microorganism of the present invention without causing no further weight increase because of lower metabolic efficiency. Because of the conversion of glucose into dietary fiber by BC-Y058 and BC-Y009 microorganism, metabolic efficiency has changed.

According to the formula represented below, the change of energy efficiency depending on feed consumption, was calculated and represented in Table 10.

energy metabolic efficiency =(weight gain(g)/amount of feeding(g)) ×1,000

Figure 3:
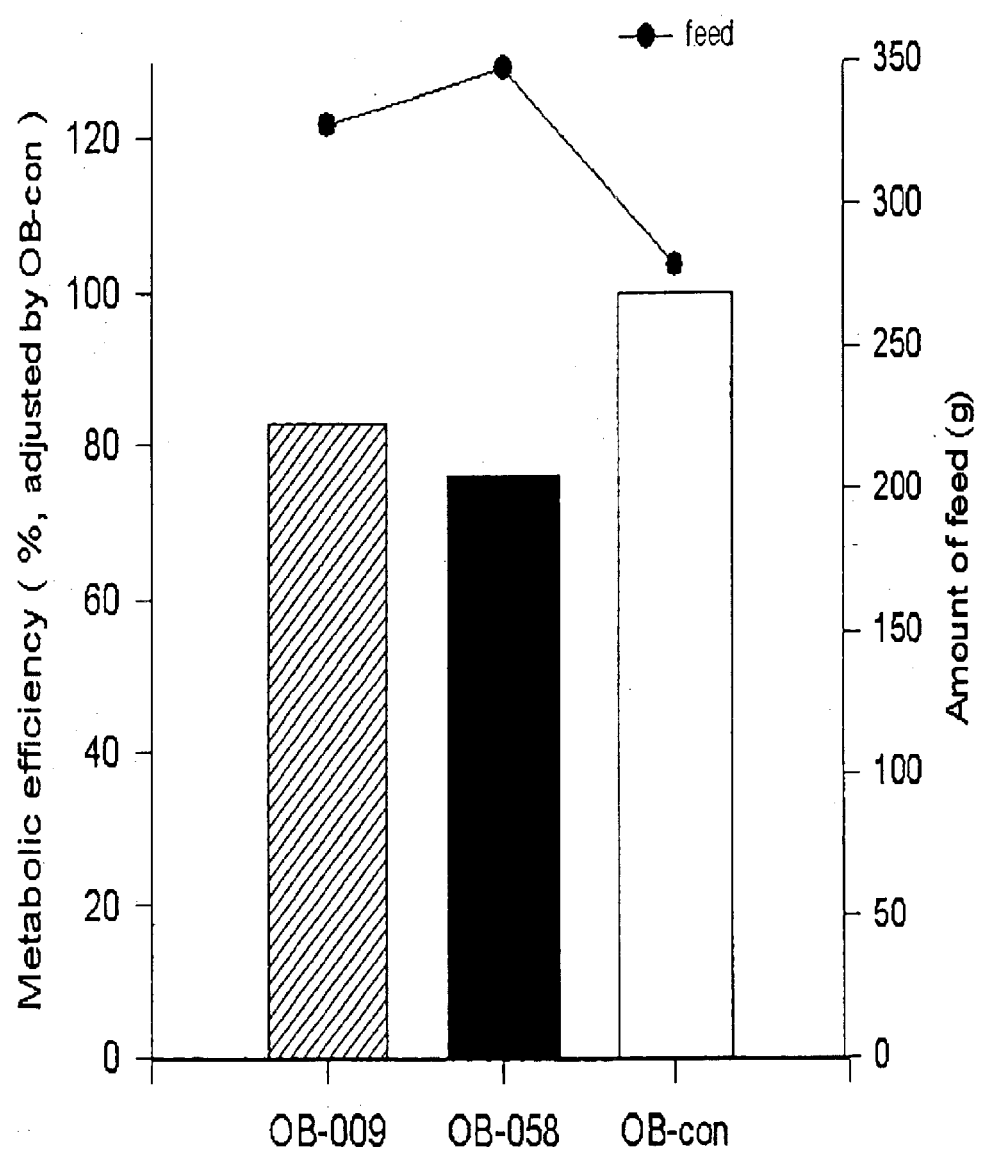
FIG. 3 is the graph illustrating the change of energy metabolism efficiency of obese mouse that has taken the microorganism of the present invention.
Figure 4:
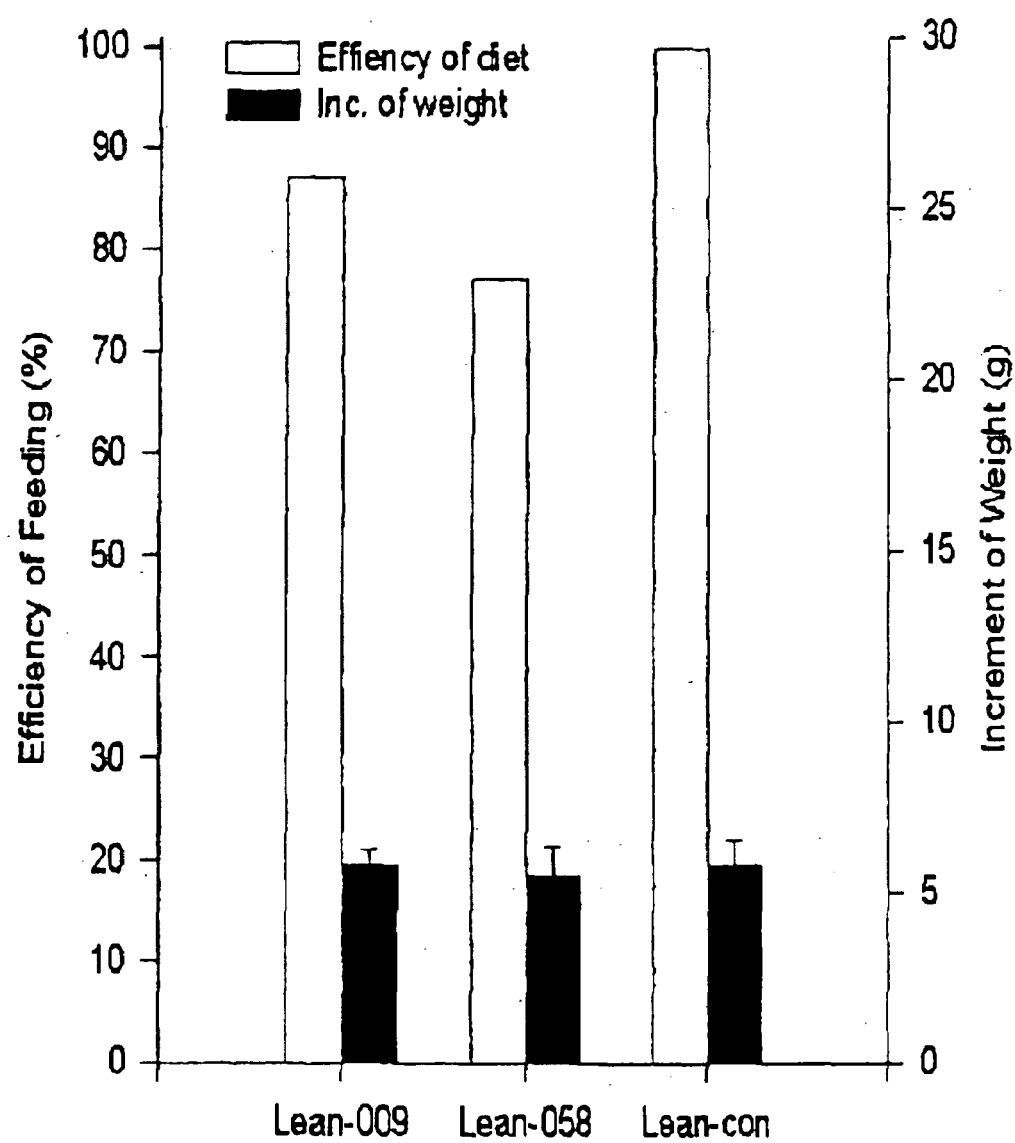
FIG. 4 is the graph illustrating the change of energy metabolism efficiency of control mouse that has taken the microorganism of the present invention.

As represented in Table 10, when microorganisms were administered to OB mouse, the energy metabolic efficiency was from 75 to 85% (FIG. 3) compared to that of the control group which was not administered with the microorganisms of the present invention (FIG. 4).

Figure 5:
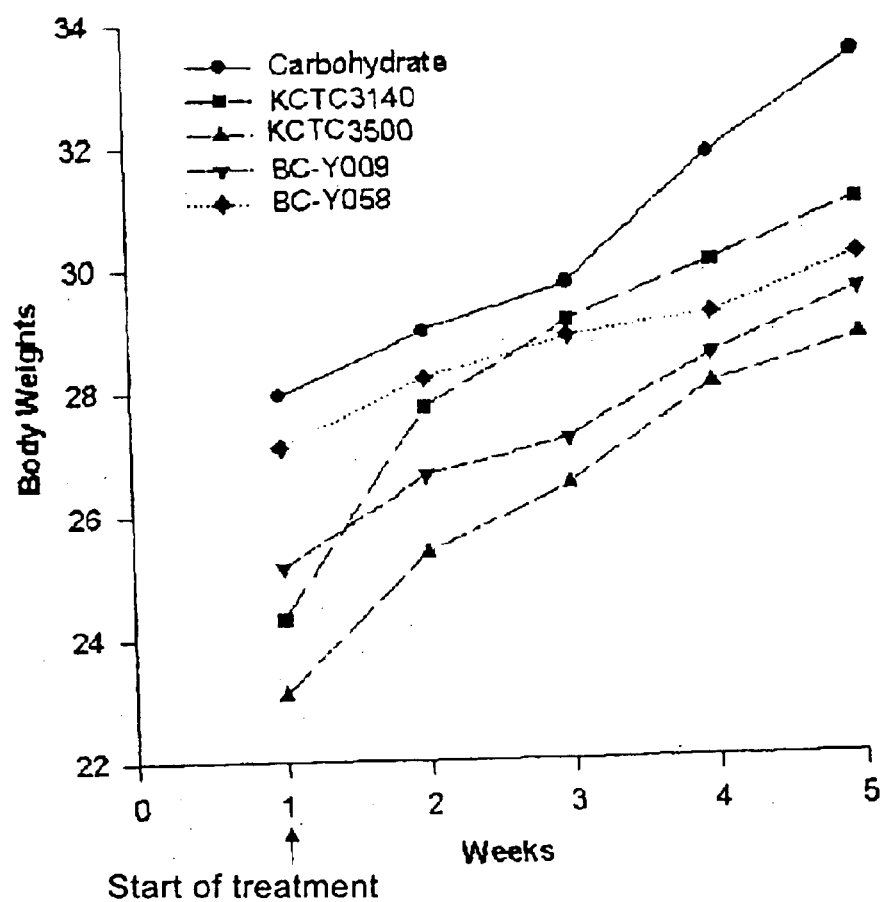
FIG. 5 is the graph illustrating the change of the body weight of obese mouse induced by pharmacological prescription.

The weight changes of mice depending on microorganisms administered with, are illustrated in FIG. 5 and it is confirmed that when *Acetobacter* BC-Y058 and *Lactobacillus* BC-Y009 were administered, the weight increase rate has decreased.

Figure 6:
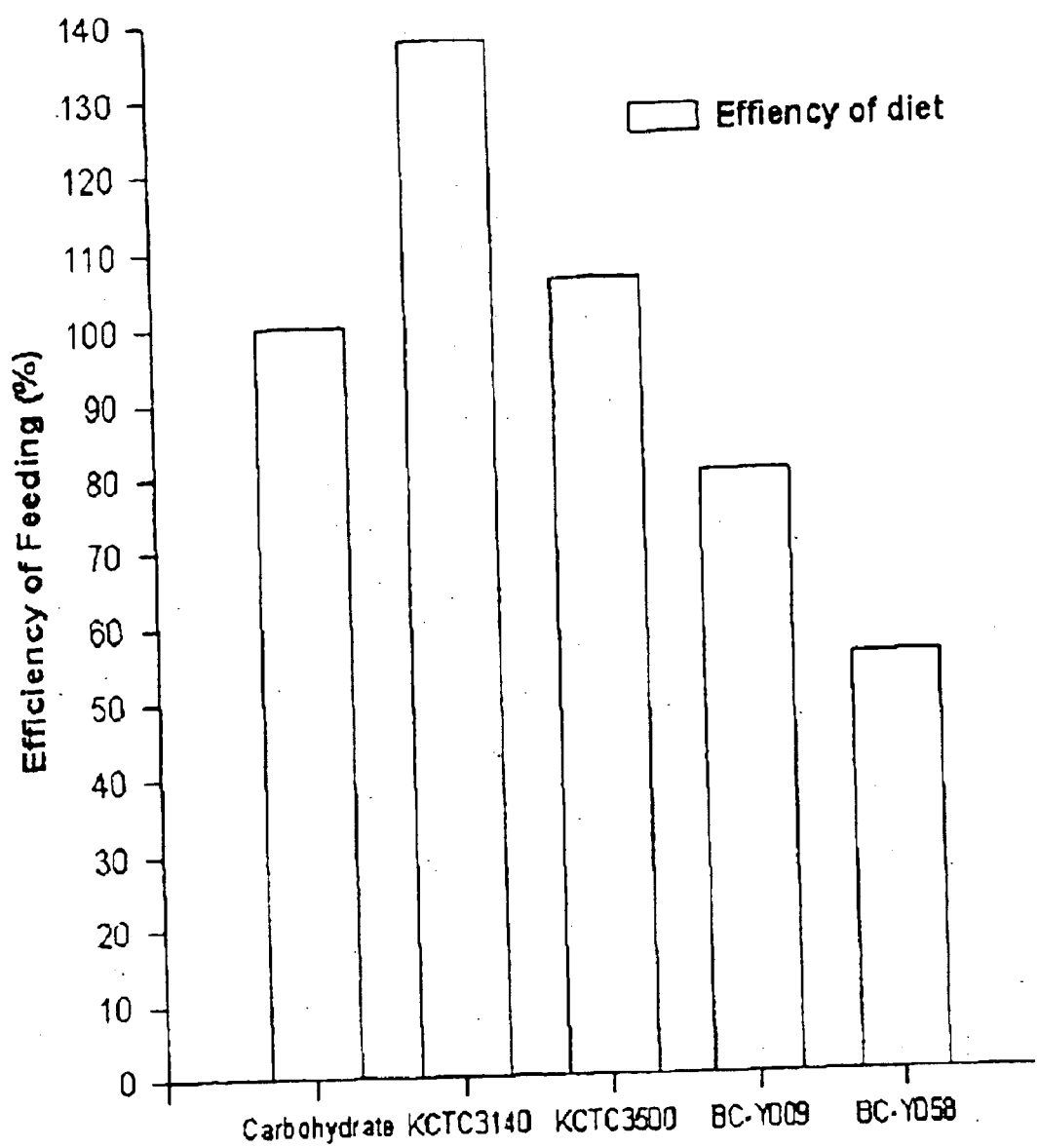
FIG. 6 is the graph illustrating the change of the metabolic efficiency of obese mouse induced by pharmacological prescription.
Figure 7:
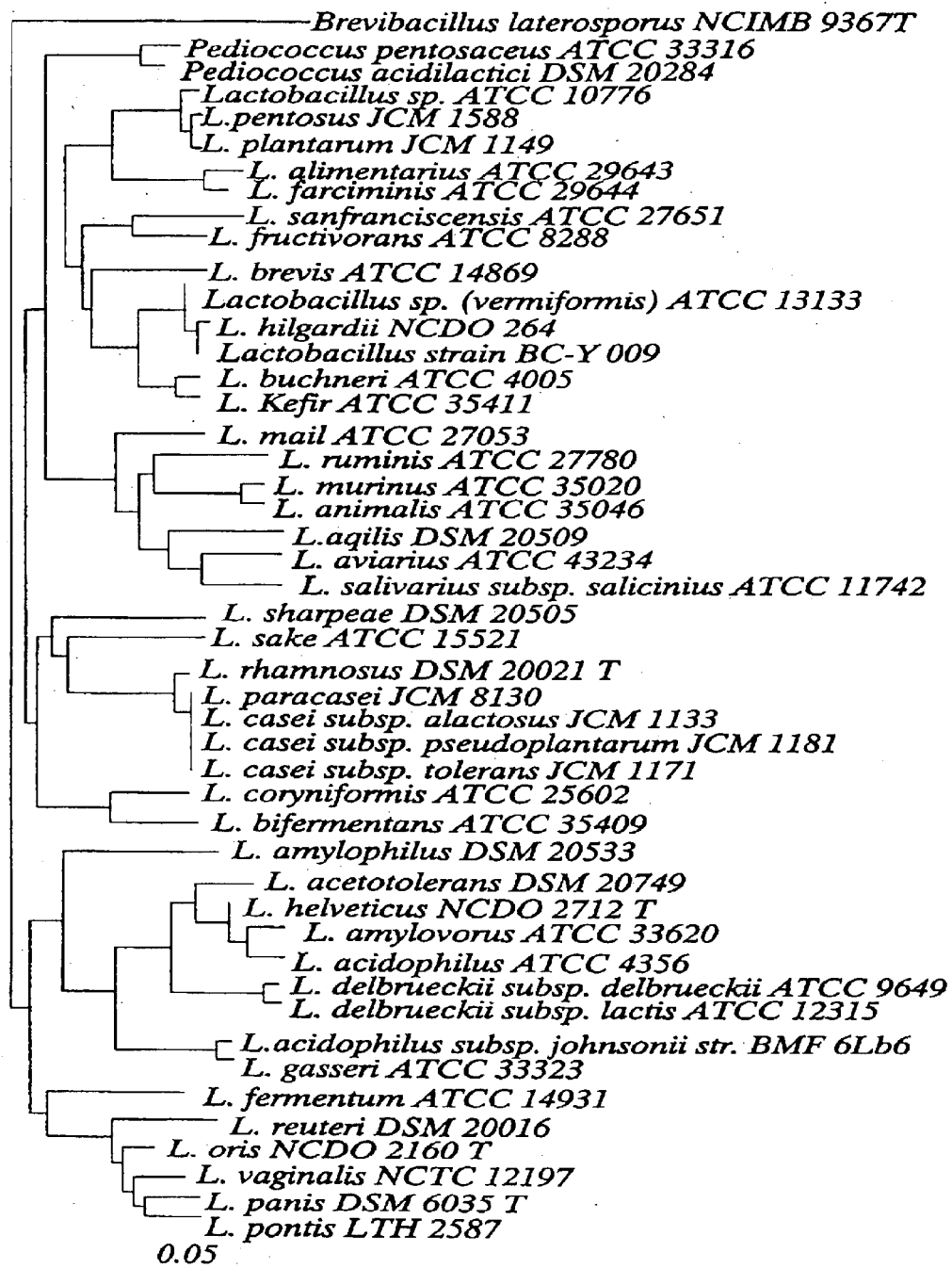
FIG. 7 is the phylogenetic analysis diagram of *Lactobacillus* BC-Y009 based on 16s rRNA nucleotide sequence of the present invention.
Figure 8:
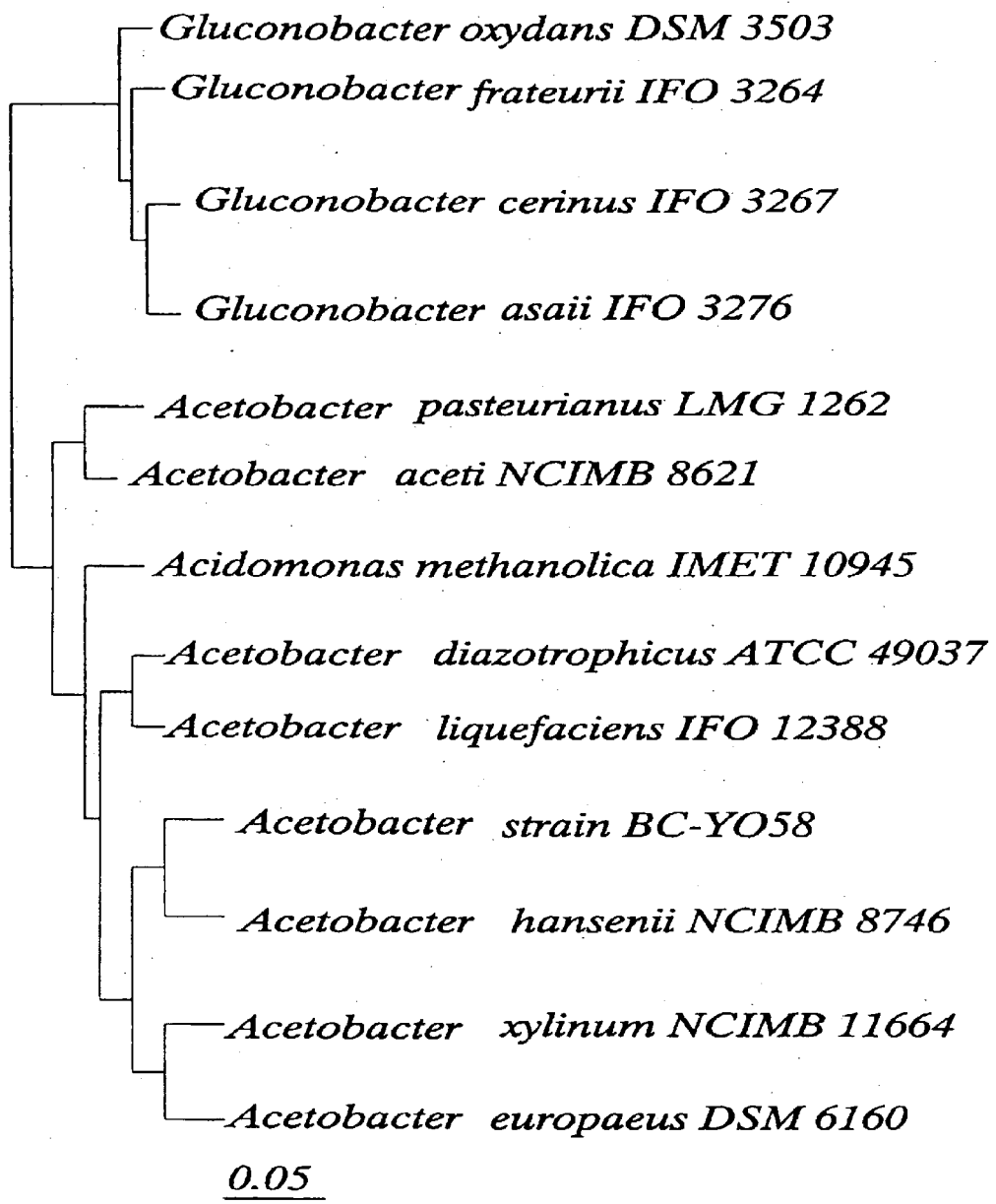
FIG. 8 is the phylogenetic analysis diagram of *Lactobacillus* BC-Y058 based on 16s rRNA nucleotide sequence of the present invention.

Additionally, as represented in Table 11 and FIG. 6, in case that KCTC3140 and KCTC3500 which consume glucose but do not produce dietary fibers, were administered, the energy efficiency of obesity-induced mice was higher than that of the control group which was not administered with the microorganisms of the present invention. However, the mouse group which was administered with BC-Y009 and BC-Y058 which produce dietary fibers, showed relatively low energy efficiency, especially in case of BC-Y058. That is the energy efficiency decreased to 55% compared with that of the control group (Table 12).

TABLE 8

Change of the mouse weight (g)

| | 1 week | 2 week | 3 week | 4 week | 5 week | 6 week | 7 week |
|---|---|---|---|---|---|---|---|
| OB-009 | 21.5 ± 3.21 | 26.53 ± 2.72 | 31.52 ±3.01 | 34.91 ± 2.5 | 37.6 ± 2.53 | 40.1 ± 1.74 | 41.4 ± 1.47 |
| OB-058 | 21.95 ± 5.3 | 26.75 ± 4.60 | 31.65 ± 2.33 | 35.8 ± 1.27 | 38.25 ±0.78 | 40.35 ± 0.64 | 41.25 ± 0.21 |
| OB-con | 21.4 ± 2.83 | 26.3 ± 1.56 | 31.9 ± 0.99 | 35.8 ± 2.12 | 38.35 ± 2.33 | 40.1 ± 2.69 | 41.75 ± 3.61 |

TABLE 9

Change of amount of feed consumption according to the administration of *Acetobacter* BC-Y058, *Lactobacillus* BC-Y009 (g)

| | 0–16 days | 16–21 days | 21–34 days | 34–41 days | Total |
|---|---|---|---|---|---|
| OB-009 | 146.3 | 32.4 | 110.7 | 38.6 | 328 |
| OB-058 | 157.4 | 34.3 | 115.3 | 41 | 348 |
| OB-con | 128.1 | 34.8 | 80.3 | 36.5 | 279.7 |

TABLE 10

Energy metabolic efficiency

| | Amount of feed (g) | weight gain (g) | energy metabolicefficiency | average weight (g) | rate of weight increase |
|---|---|---|---|---|---|
| OB-009 | 328 | 19.9 | 121 | 41.4 | 0.48 |
| OB-058 | 348 | 19.3 | 111 | 41.25 | 0.47 |
| OB-con | 279.7 | 20.35 | 146 | 41.75 | 0.49 |

EXAMPLE 8

Change of weight and diet amount of obesity mouse induced by GTG and subsequent change in metabolic efficiency Before feeding *Acetobacter* BC-Y058 and *Lactobacillus* BC-Y009, each mouse was administered with 1 g/kg of goldthioglucose (Cat. A-0632, Sigma, USA) in order to induce obesity. And every 3 or 4 weeks, weight change was measured and only obesity-induced mice were selected. For accuracy of the experiment, a mouse of which weight increase was too great or too little relatively, was excluded from the experiment.

The target was female C57BL/6J mice and breeding environment and conditions were the same as those in Example 6. The test subjects were classified into BC-Y058 group, KCTC3140 group, KCTC3500 group, and BC-Y009 group depending on microorganisms.

TABLE 11

Metabolism efficiency of obese mouse induced with drug administration (g)

| | Weight gain (g) | amount of feed (g) | energy metabolic efficiency |
|---|---|---|---|
| Carbohydrate | 5.43 | 103.7 | 52 |
| KCTC3140 | 6.65 | 92.4 | 72 |
| KCTC3500 | 5.67 | 102.2 | 55 |
| BC-Y009 | 4.38 | 104.4 | 42 |
| BC-Y058 | 2.98 | 102.7 | 29 |

EXAMPLE 9

Lipid level changes when BC-Y058 and BC-Y009 were administered

After administration of the microorganisms of the present invention, the change of blood lipid, especially cholesterol change, was analyzed and confirmed whether or not the microorganisms affected the circulatory disease, such as, artheriosclerosis and myocardial infarction besides diabetes mellitus and obesity.

Lipid analysis was performed by means of enzyme coloring method as in Example 6, using TG-glycezyme-V (Young-Yeoun Chemical Co., Japan), HDL-zyme-V (Young-Yeoun Chemical Co., Japan), Cholestezyme-V (Young-Yeoun Co., Japan), LDL cholesterol (Cat. 61532, BioMeriux, France), to measure the absorbance at 505 to 570 nm with standard solution, and the amount of lipid in blood was calculated.

As represented in Table 12, lipid concentration before feed administration did not show any differences in obese mouse. However, after *Acetobacter* BC-Y058 and *Lactobacillus* BC-Y009 were administered, as indicated in Table 12, the change of lipid concentration was apparent after 7 weeks.

In case of obese mice that have taken the microorganism, the lipid level did not change in comparison with the data of early steps in the present experiment and however, in case of control mouse which had not been administered with the microorganisms, overall lipid content in blood was increased.

TABLE 12

Lipid amount in blood before administration of feed (mg/dl)

|  | total cholesterol | TG | HDL-C | LDL-C |
|---|---|---|---|---|
| OB-009 | 130.22 ± 4.11 | 98.1 ± 11.4 | 98.73 ± 9.7 | 4.13 ± 2.36 |
| OB-058 | 129.37 ± 4.24 | 101.6 ± 10.36 | 113.52 ± 15.47 | 3.35 ± 2.08 |
| OB-con | 127.57 ± 4.32 | 97.13 ± 14.64 | 96.86 ± 7.61 | 6.62 ± 2.78 | n = 4
TG: Triglyceride
HDL-C: High Density Lipoprotein Cholesterol
LDL-C: Low Density Lipoprotein Cholesterol

TABLE 13

Lipid amount in blood after administration of feed (mg/dl)

|  | Total cholesterol | TG | HDL-C | LDL-C |
|---|---|---|---|---|
| OB-009 | 167.04 ± 1.12 | 100.76 ± 3.2 | 157.71 ± 2.4 | 4.2 ± 2.08 |
| OB-058 | *135.25 ± 2.47 | 98.5 ± 2.83 | 135 ± 1.41 | 3.36 ± 1.31 |
| OB-con | *174 ± 1.41 | 110.5 ± 1.06 | 165.25 ± 1.06 | 3.19 ± 0.36 | n = 4, *p < 0.05
TG: Triglyceride
HDL-C: High Density Lipoprotein Cholesterol
LDL-C: Low Density Lipoprotein Cholesterol The industrial applicability of the present invention The microorganisms of the present invention are capable of living within the intestine and converting monosaccharides and disaccharides into high molecular weight materials which cannot be absorbed and hardly digestible in the intestine, thereby remarkably reducing the amount of monosaccharide to be absorbed. Therefore, the energy required for metabolic activity is provided from lipids and protein accumulated in the body, thus effectively suppressing obesity and diabetes mellitus. In addition, the microorganisms of the present invention produce dietary fibers within the intestine and excreting harmful materials along with these dietary fibers, to prevent appendicitis or large intestinal cancer, to suppress cholesterol absorption and to clean the intestine.

While the present invention has been particularly shown and described with reference to particular examples thereof, it will be understood by those skilled in the art that various changes in form and details may be conceived therefrom without departing from the spirit and scope of the present invention as defined by the appended claims.

This application claims priority from the Korean Patent Application Nos. 10-2000-0026379 (filed May 17, 2000) and 10-2000-0049805 (filed Aug. 26, 2000), the contents of which are hereby incorporated by reference in their entirety, including the specification, drawings and claims.

What is claimed is:

1. A biologically pure strain of *Lactobacillus* sp. BC-Y009 (KCTC-774BP).

2. A biologically pure strain of *Acetobacter* sp. BC-Y058 (KCTC-773BP).

3. A pharmaceutical composition comprising at least one microorganism selected from the group consisting of *Acetobacter* BC-Y058 and *Lactobacillus* in an amount effective to treat obesity and a pharmaceutically acceptable carrier.

4. The pharmaceutical composition according to claim 3, which is a formulation suitable for oral administration.

5. The pharmaceutical composition according to claim 3, which is a formulation coated with enteric coating materials.

6. The pharmaceutical composition according to claim 4, which is a formulation coated with enteric coating materials.

7. A pharmaceutical composition comprising at least one microorganism selected from the group consisting of *Acetobacter* BC-Y058 and *Lactobacillus* C-Y009 in an amount effective to treat diabetes mellitus and a pharmaceutically acceptable carrier.

8. The pharmaceutical composition according to claim 7, which is a formulation suitable for oral administration.

9. The pharmaceutical composition according to claim 7, which is a formulation coated with enteric coating materials.

10. A method for treating obesity, comprising administering to a subject in need thereof a pharmaceutical composition comprising at least one microorganism selected from the group consisting of *Acetobacter* BC-Y058 and *Lactobacillus* BC-Y009 in an amount effective to treat obesity and a pharmaceutically acceptable carrier.

11. The method according to claim 10, wherein the pharmaceutical composition is a formulation suitable for oral administration.

12. The method according to claim 11, wherein the pharmaceutical composition is a formulation coated with enteric coating materials.

13. The method according to claim 10, wherein the pharmaceutical composition is a formulation coated with enteric coating material.

14. A method for treating diabetes mellitus, corn rising administering to a subject in need thereof a pharmaceutical composition comprising at east one microorganism selected from the group consisting of *Acetobacter* BC-Y058 and *Lactobacillus* BC-Y009 in an amount effective to treat diabetes mellitus and a pharmaceutically acceptable carrier.

15. The method according to claim 14, wherein the pharmaceutical composition is a formulation suitable for oral administration.

16. The method according to claim 14, wherein the pharmaceutical composition is a formulation coated with enteric coating materials.

17. A method for controlling weight gain, comprising administering to a subject in need thereof a pharmaceutical composition comprising at least one microorganism selected from the group consisting of *Acetobacter* BC-Y058 and *Lactobacillus* BC-Y009 in an effective amount and a pharmaceutically acceptable carrier.

18. The method according to claim 17, wherein the pharmaceutical composition is suitable for oral administration.

19. The method according to claim 17, wherein the pharmaceutical composition is coated with enteric coating materials.

20. A method for controlling blood glucose level, comprising administering to a subject in need thereof a pharmaceutical composition comprising at least one microorganism selected from the group consisting of *Acetobacter* BC-Y058 and *Lactobacillus* BC-Y009 in an effective amount and a pharmaceutically acceptable carrier.

21. The method according to claim 20, wherein the pharmaceutical composition is suitable for oral administration.

22. The method according to claim 20, wherein the pharmaceutical composition is coated with enteric coating materials.

23. The method according to claim 20, wherein a normal blood glucose level is not affected.

24. A method for controlling absorption of blood lipid, comprising administering to a subject in need thereof a pharmaceutical composition comprising at least one microorganism selected from the group consisting of *Acetobacter* C-Y058 and *Lactobacillus* BC-Y009 in an effective amount and a pharmaceutically acceptable carrier.

25. The method according to claim 24, wherein the pharmaceutical composition is suitable for oral administration.

26. The method according to claim 24, wherein the pharmaceutical composition is coated with enteric coating materials.

* * * * *